United States Patent
Magee et al.

(10) Patent No.: US 9,757,200 B2
(45) Date of Patent: Sep. 12, 2017

(54) INTELLIGENT CATHETER

(71) Applicant: The Spectranetics Corporation, Colorado Springs, CO (US)

(72) Inventors: Matthew Miles Magee, Monument, CO (US); Paul Andrew Hollendorfer, Colorado Springs, CO (US)

(73) Assignee: The Spectranetics Corporation, Colorado Springs, CO (US)

( * ) Notice: Subject to any disclaimer, the term of this patent is extended or adjusted under 35 U.S.C. 154(b) by 270 days.

(21) Appl. No.: 13/804,812

(22) Filed: Mar. 14, 2013

(65) Prior Publication Data

US 2014/0276603 A1 Sep. 18, 2014

(51) Int. Cl.
| | |
|---|---|
| *A61B 90/98* | (2016.01) |
| *A61B 19/00* | (2006.01) |
| *A61M 25/00* | (2006.01) |
| *A61B 90/90* | (2016.01) |

(52) U.S. Cl.
CPC .............. *A61B 19/44* (2013.01); *A61B 90/90* (2016.02); *A61B 90/98* (2016.02); *A61M 25/00* (2013.01); *A61M 2205/60* (2013.01); *A61M 2205/6009* (2013.01); *A61M 2205/6018* (2013.01)

(58) Field of Classification Search
CPC .............. A61B 19/44; A61B 2019/448; A61B 1/00059; A61B 2018/00988; A61B 2019/4826; A61B 18/24; A61B 90/90; A61B 90/98; A61M 2205/27; A61M 2205/3592; A61M 2205/60; A61M 2205/6009; A61M 2205/6018; A61M 25/00; G06K 19/07749; G06K 2017/009; G06F 19/3406

See application file for complete search history.

(56) References Cited

U.S. PATENT DOCUMENTS

| | | | |
|---|---|---|---|
| 4,053,845 | A | 10/1977 | Gould |
| 4,641,912 | A | 2/1987 | Goldenberg |
| 4,669,465 | A | 6/1987 | Moore et al. |
| 4,686,979 | A | 8/1987 | Gruen et al. |
| 4,732,448 | A | 3/1988 | Goldenberg |
| 4,747,405 | A | 5/1988 | Leckrone |
| 4,769,005 | A | 9/1988 | Ginsburg et al. |

(Continued)

FOREIGN PATENT DOCUMENTS

| | | |
|---|---|---|
| EP | 0211984 B2 | 3/1987 |
| EP | 2319404 B1 | 5/2011 |

(Continued)

OTHER PUBLICATIONS

Griffin et al. Calibration and Mapping of a Human Hand for Dexterous Telemanipulation; ASME IMECE Conference, 2000, 8 pages.

(Continued)

*Primary Examiner* — Nay Tun
(74) *Attorney, Agent, or Firm* — Faegre Baker Daniels LLP

(57) ABSTRACT

A system includes a microprocessor executable verification module in a base unit and a microprocessor readable identifier of an endovascular device in a memory of the endovascular device. The microprocessor executable verification module, based on the identifier, at least one of configures the endovascular device for use and determines whether the endovascular device can be enabled for use.

21 Claims, 7 Drawing Sheets

(56) References Cited

U.S. PATENT DOCUMENTS

| | | | |
|---|---|---|---|
| 4,784,132 A | 11/1988 | Fox et al. | |
| 4,788,975 A | 12/1988 | Shturman et al. | |
| 4,799,754 A | 1/1989 | Goldenberg | |
| 4,807,620 A | 2/1989 | Strul et al. | |
| 4,830,460 A | 5/1989 | Goldenberg | |
| 4,844,062 A | 7/1989 | Wells | |
| 4,848,336 A | 7/1989 | Fox et al. | |
| 4,850,686 A | 7/1989 | Morimoto et al. | |
| 4,913,142 A | 4/1990 | Kittrell et al. | |
| 4,919,508 A | 4/1990 | Grace et al. | |
| 4,924,863 A | 5/1990 | Sterzer | |
| 4,925,265 A | 5/1990 | Rink et al. | |
| 5,016,964 A | 5/1991 | Donnelly | |
| 5,024,234 A | 6/1991 | Leary et al. | |
| 5,026,366 A | 6/1991 | Leckrone | |
| 5,034,010 A | 7/1991 | Kittrell et al. | |
| 5,040,548 A | 8/1991 | Yock | |
| 5,041,108 A | 8/1991 | Fox et al. | |
| 5,047,952 A | 9/1991 | Kramer et al. | |
| 5,154,680 A | 10/1992 | Drzewiecki et al. | |
| 5,165,897 A | 11/1992 | Johnson | |
| 5,176,674 A | 1/1993 | Hofmann | |
| 5,188,632 A | 2/1993 | Goldenberg | |
| 5,207,672 A | 5/1993 | Roth et al. | |
| 5,217,454 A | 6/1993 | Khoury | |
| 5,250,045 A | 10/1993 | Bohley | |
| 5,263,953 A | 11/1993 | Bagby | |
| 5,267,341 A | 11/1993 | Shearin | |
| 5,300,085 A | 4/1994 | Yock | |
| 5,304,171 A | 4/1994 | Gregory et al. | |
| 5,318,032 A | 6/1994 | Lonsbury et al. | |
| 5,350,375 A | 9/1994 | Deckelbaum et al. | |
| 5,350,377 A | 9/1994 | Winston et al. | |
| 5,350,395 A | 9/1994 | Yock | |
| 5,352,197 A | 10/1994 | Hammersmark et al. | |
| 5,377,683 A | 1/1995 | Barken | |
| 5,395,361 A | 3/1995 | Fox et al. | |
| 5,400,428 A | 3/1995 | Grace | |
| 5,415,653 A | 5/1995 | Wardle et al. | |
| 5,423,740 A | 6/1995 | Sullivan et al. | |
| 5,425,355 A | 6/1995 | Kulick | |
| 5,429,604 A | 7/1995 | Hammersmark et al. | |
| 5,429,617 A | 7/1995 | Hammersmark et al. | |
| 5,440,664 A | 8/1995 | Harrington et al. | |
| 5,451,233 A | 9/1995 | Yock | |
| 5,456,680 A | 10/1995 | Taylor et al. | |
| 5,464,395 A | 11/1995 | Faxon et al. | |
| 5,470,330 A | 11/1995 | Goldenberg et al. | |
| 5,484,433 A | 1/1996 | Taylor et al. | |
| 5,492,131 A | 2/1996 | Galel | |
| 5,514,128 A | 5/1996 | Hillsman et al. | |
| 5,536,242 A | 7/1996 | Willard et al. | |
| 5,571,151 A | 11/1996 | Gregory | |
| 5,573,531 A | 11/1996 | Gregory | |
| 5,623,940 A | 4/1997 | Daikuzono | |
| 5,643,251 A | 7/1997 | Hillsman et al. | |
| 5,649,923 A | 7/1997 | Gregory et al. | |
| 5,657,760 A | 8/1997 | Ying et al. | |
| 5,722,972 A | 3/1998 | Power et al. | |
| 5,755,714 A | 5/1998 | Murphy-Chutorian | |
| 5,792,118 A | 8/1998 | Kurth et al. | |
| 5,800,350 A | 9/1998 | Coppleson et al. | |
| 5,803,083 A | 9/1998 | Buck et al. | |
| 5,807,377 A | 9/1998 | Madhani et al. | |
| 5,817,144 A | 10/1998 | Gregory | |
| 5,824,026 A | 10/1998 | Diaz | |
| 5,830,209 A | 11/1998 | Savage et al. | |
| 5,836,946 A | 11/1998 | Diaz et al. | |
| RE36,104 E | 2/1999 | Solar | |
| 5,891,133 A | 4/1999 | Murphy-Chutorian | |
| 5,938,609 A | 8/1999 | Pomeranz | |
| 5,976,124 A | 11/1999 | Reiser | |
| 5,986,643 A | 11/1999 | Harvill et al. | |
| 5,989,243 A | 11/1999 | Goldenberg | |
| 6,022,342 A | 2/2000 | Mukherjee | |
| 6,033,402 A | 3/2000 | Tu et al. | |
| 6,036,715 A | 3/2000 | Yock | |
| 6,056,743 A | 5/2000 | Ellis et al. | |
| 6,066,130 A | 5/2000 | Gregory et al. | |
| 6,117,128 A | 9/2000 | Gregory | |
| 6,231,563 B1 | 5/2001 | White et al. | |
| 6,287,297 B1 | 9/2001 | Woodruff et al. | |
| 6,290,668 B1 | 9/2001 | Gregory et al. | |
| 6,302,875 B1 | 10/2001 | Makower et al. | |
| 6,370,411 B1* | 4/2002 | Osadchy et al. | 600/372 |
| 6,419,684 B1 | 7/2002 | Heisler et al. | |
| 6,432,115 B1 | 8/2002 | Mollenauer et al. | |
| 6,447,504 B1 | 9/2002 | Ben-Haim et al. | |
| 6,447,525 B2 | 9/2002 | Follmer et al. | |
| 6,458,098 B1 | 10/2002 | Kanesaka | |
| 6,539,132 B2 | 3/2003 | Ivtsenkov et al. | |
| 6,575,993 B1 | 6/2003 | Yock | |
| 6,597,829 B2 | 7/2003 | Cormack | |
| 6,733,495 B1* | 5/2004 | Bek et al. | 606/34 |
| 6,743,208 B1 | 6/2004 | Coyle | |
| 6,792,390 B1* | 9/2004 | Burnside et al. | 702/183 |
| 7,238,178 B2 | 7/2007 | Maschke | |
| 7,319,566 B2 | 1/2008 | Prince et al. | |
| 7,568,619 B2* | 8/2009 | Todd et al. | 235/385 |
| 7,572,254 B2 | 8/2009 | Hebert et al. | |
| 7,846,153 B2 | 12/2010 | Hebert et al. | |
| 7,930,065 B2 | 4/2011 | Larkin et al. | |
| 7,959,608 B2 | 6/2011 | Nash et al. | |
| 7,988,633 B2* | 8/2011 | Hossack et al. | 600/467 |
| 8,016,745 B2 | 9/2011 | Hassler et al. | |
| 8,016,748 B2 | 9/2011 | Mourlas et al. | |
| 8,050,739 B2 | 11/2011 | Eck et al. | |
| 8,100,893 B2* | 1/2012 | Dadisman | 606/15 |
| 8,361,097 B2 | 1/2013 | Patel et al. | |
| 8,545,488 B2 | 10/2013 | Taylor et al. | |
| 8,628,519 B2 | 1/2014 | Taylor et al. | |
| 2001/0014805 A1 | 8/2001 | Burbank et al. | |
| 2002/0013572 A1 | 1/2002 | Berlin | |
| 2002/0026118 A1 | 2/2002 | Govari | |
| 2002/0045811 A1 | 4/2002 | Kittrell et al. | |
| 2002/0103459 A1 | 8/2002 | Sparks et al. | |
| 2002/0107445 A1 | 8/2002 | Govari | |
| 2002/0159685 A1 | 10/2002 | Cormack | |
| 2003/0032936 A1 | 2/2003 | Lederman | |
| 2003/0045798 A1 | 3/2003 | Hular et al. | |
| 2003/0078566 A1 | 4/2003 | Elliott et al. | |
| 2003/0204185 A1* | 10/2003 | Sherman et al. | 606/41 |
| 2003/0219202 A1 | 11/2003 | Loeb et al. | |
| 2004/0010204 A1 | 1/2004 | Weber et al. | |
| 2004/0057659 A1 | 3/2004 | Baugh | |
| 2004/0059280 A1 | 3/2004 | Makower et al. | |
| 2004/0075919 A1 | 4/2004 | Diaz et al. | |
| 2004/0111016 A1 | 6/2004 | Casscells et al. | |
| 2004/0127889 A1 | 7/2004 | Zhang et al. | |
| 2004/0133154 A1 | 7/2004 | Flaherty et al. | |
| 2004/0162548 A1 | 8/2004 | Reiser | |
| 2005/0004453 A1 | 1/2005 | Tearney et al. | |
| 2005/0149176 A1 | 7/2005 | Heggestuen et al. | |
| 2005/0203416 A1 | 9/2005 | Angelsen et al. | |
| 2006/0020260 A1 | 1/2006 | Dover et al. | |
| 2006/0094930 A1 | 5/2006 | Sparks et al. | |
| 2006/0217695 A1 | 9/2006 | DeBenedictis et al. | |
| 2006/0247532 A1 | 11/2006 | Ramanujam et al. | |
| 2007/0060879 A1 | 3/2007 | Weitzner et al. | |
| 2007/0106289 A1 | 5/2007 | O'Sullivan | |
| 2007/0115152 A1 | 5/2007 | Bjorklund et al. | |
| 2008/0019671 A1 | 1/2008 | Maitland et al. | |
| 2008/0058629 A1 | 3/2008 | Seibel et al. | |
| 2008/0106388 A1* | 5/2008 | Knight | A61M 5/31511 340/10.42 |
| 2008/0108867 A1 | 5/2008 | Zhou | |
| 2008/0154296 A1 | 6/2008 | Taylor et al. | |
| 2009/0177095 A1 | 7/2009 | Aeby et al. | |
| 2009/0203989 A1 | 8/2009 | Burnside et al. | |
| 2010/0114081 A1 | 5/2010 | Keeler et al. | |
| 2010/0152717 A1 | 6/2010 | Keeler | |
| 2010/0200076 A1 | 8/2010 | Hieb et al. | |
| 2011/0160681 A1* | 6/2011 | Dacey, Jr. | A61L 2/0011 604/265 |

(56) References Cited

U.S. PATENT DOCUMENTS

| | | | |
|---|---|---|---|
| 2011/0196291 A1* | 8/2011 | Vischer et al. | 604/74 |
| 2011/0224649 A1* | 9/2011 | Duane et al. | 604/523 |
| 2011/0270091 A1* | 11/2011 | Hossack et al. | 600/463 |
| 2012/0181331 A1* | 7/2012 | Beden et al. | 235/375 |
| 2012/0253360 A1 | 10/2012 | White et al. | |
| 2012/0302828 A1 | 11/2012 | Toledo-Crow et al. | |
| 2013/0131579 A1* | 5/2013 | Mantell et al. | 604/23 |
| 2013/0253490 A1 | 9/2013 | Bitzer et al. | |
| 2013/0338500 A1 | 12/2013 | Taylor et al. | |
| 2014/0114298 A1 | 4/2014 | Taylor et al. | |
| 2014/0275982 A1 | 9/2014 | Hendrick et al. | |
| 2014/0276689 A1 | 9/2014 | Grace | |
| 2014/0276690 A1 | 9/2014 | Grace | |
| 2015/0011843 A1 | 1/2015 | Toth et al. | |

FOREIGN PATENT DOCUMENTS

| | | |
|---|---|---|
| GB | 2208807 A | 4/1989 |
| WO | 9819614 A1 | 5/1998 |
| WO | WO0057228 A2 | 9/2000 |
| WO | 2007115152 A2 | 10/2007 |
| WO | 2010042249 A4 | 8/2010 |

OTHER PUBLICATIONS

Hager-Ross et al. Quantifying the Independence of Human Finger Movements: Comparisons of Digits, Hands, and Movement Frequencies; The Journal of Neurosciences, vol. 20 No. 22, Nov. 15, 2000, pp. 8542-8550.

Hajjarian et al. Intravascular Laser Speckle Imaging Catheter for the Mechanical Evaluation of the Arterial Wall; Journal of Biomedical Optics vol. 16(2) Feb. 2011, 7 pages.

Hanke et al. Morphological Changes and Smooth Muscle Cell Proliferation After Experimental Excimer Laser Treatment; Circulation vol. 83, 1991 pp. 1380-1389.

Hattori et al. InVivo Raman Study of the Living Rat Esophagus and Stomach Using a Micro-Raman Probe Under an Endoscope; Applied Spectroscopy vol. 61, No. 6, 2007, 8 pages.

Hauser Deaths and Cardiovascular Injuries Due to Device-Assisted Implantable Cardioverter-Defibrillator and Pacemaker Lead Extraction; Europace vol. 12, 2010, pp. 395-401.

Henning et al. An In Vivo Strain Gage Study of Elongation of the Anterior Cruciate Ligament; The American Journal of Sports Medicine, vol. 13, No. 1m 1985, pp. 22-26.

Inmann et al. An Instrument Object for Evaluation of Lateral Hand Grasp During Functional Tasks; Journal of Medical Engineering & Technology, vol. 25. No. 5, Sep./Oct. 2001, pp. 207-211.

Insull The Pathology of Atherosclerosis; Plaque Development and Plaque Responses to Medical Treatment; The American Journal of Medicine, vol. 122, No. 1A, Jan. 2009, 12 pages.

Jagsi et al. Original Investigation: Residents Report on Adverse Events and Their Causes; Arch Intern Med/ vol. 163 Dec. 12/26, 2005 7 pages.

Johns et al. Determination of Reduced Scattering Coefficient of Biological Tissue From a Needle-Like Probe; Optics Express vol. 13, No. 13. Jun. 27, 2005 pp. 4828-4842.

Kane et al. A Traction Stress Sensor Array for Use in High-Resolution Robotic Tactile Imaging; Journal of Microelectromechanical Systems, vol. 9, No. 4, Dec. 2000, pp. 425-434.

Kang et al. A Carbon Nanotube Strain Sensor for Structural Health Monitoring; Smart Matter. Struct. vol. 15, 2006, pp. 737-748.

Karimov et al. A Carbon Nanotube-Based Pressure Sensor, Phys. Scr. 83, 2011, 5 pages.

Karsch et al. Percutaneous Coronary Excimer Laser Angioplasty Initial Clinical Results; The Lancet, Sep. 16, 1989 pp. 647-650.

Kennergren Excimer Laser Assisted Extraction of Permanent Pacemaker and ICD Leads: Present Experiences of a European Multi-Centre Study; European Journal of Cardio-Thoracic Surgery 15, 1990, pp. 856-860.

Khairy et al. Laser Lead Extraction in Adult Congenital Heart Disease; J. Cardiovasc Electrophysiol, vol. 18, 2006, pp. 507-511.

Khalil et al. Tissue Elasticity Estimation With Optical Coherence Elastography: Toward Mechanical Characterization of In Vivo Soft Tissue; Annals of Biomedical Engineering, vol. 33, No. 11, Nov. 2005, pp. 1631-1639.

Kochiadakis et al. The Role of Laser-Induced Fluorescence in Myocardial Tissue Characterization: An Experimental InVitro Study; Chest vol. 120, 2001, pp. 233-239.

Koulouris et al. Intravascular Lead Extractions: Tips and Tricks; Intech Open Science/Open Minds http//creativecommons.org/licenses/by/3.0, 2012 pp. 189-216.

Kremers et al. The National ICD Registry Report: Version 2.1 Including Leads and Pediatrics for Years 2010 and 2011; pp. 59-65.

Lathan et al. The Effects of Operator Spatial Perception and Sensory Feedback on Human-Robot Teleoperation Performance; Presence, vol. 11, No. 4, Aug. 2002, 368-377.

Levine et al. 2011 ACCF/AHA/SCAI Guideline for Percutaneous Coronary Intervention: Executive Summary; Journal of the American College of Cardiology vol. 58, No. 24, 2011, pp. 2250-2583.

Li et al. Strain and Pressure Sensing Using Single-Walled Carbon Nanotubes; Nanotechnology vol. 15, 2004, pp. 1493-1496.

Lieber et al. Sarcomere Length Determination Using Laser Diffraction: Effect of Beam and Fiber Diameter; Biophys J. vol. 45, May 1984, pp. 1007-1016.

Lipomi et al. Skin-Like Pressure and Strain Sensors Based on Transparent Elastic Films of Carbon Nanotubes; Nature Nanotechnology, vol. 6, Dec. 2011, pp. 788-792.

Maréchal, L. et al. "Measurement System for Gesture Characterization During Chest Physiotherapy Act on Newborn Babies Suffering from Bronchiolitis." Proceedings of the 29th Annual International Conference of the IEEE EMBS, Cité Internationale, Lyon, France. Aug. 23-26, 2007. pp. 5770-5773.

Maytin et al. Multicenter Experience With Extraction of the Sprint Fidelis Implantable Cardioverter-Defibrillator Lead; Journal of the American College of Cardiology vol. 56, No. 8, 2010, pp. 642-646.

Maytin et al. The Challenges of Transvenous Lead Extraction; Heart vol. 97, 2011, pp. 425-434.

Medtronic's Brochure; Implantable Pacemaker and Defibrillator Information; Apr. 2006, 2 pages.

Meier-Ewert et al. Endocardial Pacemaker or Defibrillator Leads With Infected Vegetations: A Single-Center Experience and Consequences of Transvenous Extraction; AM Heart Journal vol. 146, 2003, pp. 339-344.

Menciassi et al. Force Sensing Microinstrument for Measuring Tissue Properties and Pulse in Microsurgery, IEEE/ASME Transactions on Mechatronics, vol. 8, No. 1, Mar. 2003, pp. 10-17.

Mishra et al. Fiber Grating Sensors in Medicine: Current and Emerging Applications; Sensors and Actualtors A, 167, 2011, pp. 279-290.

Missinne Flexible Miniature Shear Sensors for Prosthetics; SPIE Newsroom SPIE, May 13, 2013, 4 pages.

Missinne, Jeroen et al. "Embedded Flexible Optical Shear Sensor." IEEE Sensors 2010 Conference. 2010. pp. 987-990.

Mond et al. The Electrode-Tissue Interface: The Revolutionary Role of Steroid Elution; Pace vol. 15, Jan. 1992, pp. 95-107.

Moscato et al. A Micromachined Intensity-Modulated Fiber Optic Sensor for Strain Measurements: Working Principle and Static Calibration; 34th Annual International Conference of the IEEE EMBS, 2012, pp. 5790-5793.

Mujat et al.; Automated Algorithm for Breast Tissue Differentiation in Optical Coherence Tomogrpahy; Journal of Biomedical Optics 14(3), 2009, 9 pages.

Neuzil et al. Pacemaker and ICD Lead Extraction With Electrosurgical Dissection Sheaths and Standard Transvenous Extraction Systems: Results of a Randomized Trial; Europace 9 , 2007, pp. 98-104.

Nikonovas et al. The Application of Force-Sensing Resistor Sensors for Measuring Forces Developed by the Human Hand; Proc. Instn Mech Engrs. vol. 218 Part H, 2004, 9 pages.

Nilsson et al Near Infrared Diffuse Reflection and Laser-Induced Fluorescence Spectroscopy for Myocardial Tissue Characterization; Spectrochimica ACTA Part A 53, 1997, pp. 1901-1912.

(56) References Cited

OTHER PUBLICATIONS

Noble et al. High Energy Excimer Laser to Treat Coronary In-Stent Restenosis in an Under Expanded Stent; Catheter and Cardiovascular Interventions vol. 71, 2008, pp. 803-807.
Noonan et al. A Dual-Function Wheeled Probe for Tissue Viscoelastic Property Identification During Minimally Invasive Surgery; IEEE International Conference on Robotics and Automation, Apr. 10-14, 2007, 6 pages.
Okumura et al. A Systematic Analysis of In Vivo Contact Forces on Virtual Catheter Tip/Tissue Surface Contact During Cardiac Mapping and Intervention; J. Cardiovasc Electrophysiol, vol. 19, Jun. 2008, pp. 632-640.
Orengo et al. Characterization of Piezoresistive Sensors for Goniometric Glove in Hand Prostheses; Wireless VITAE, 2009 pp. 684-687.
Park et al. Exoskeletal Force-Sensing End-Effectors With Embedded Optical Fiber-Bragg Grating Sensors; IEEE Transactions on Robotics, vol. 25, No. 6, Dec. 2009, pp. 1319-1331.
Park et al. Fingertip Force Control With Embedded Fiber Bragg Grating Sensors; IEEE conference on Robotics and Automation, May 19-23, 2008, pp. 3431-3436.
Park et al. Force Sensing Robot Fingers Using Embedded Fiber Bragg Grating Sensors and Shape Deposition Manufacturing; ; IEEE International Conference on Robotics and Automation, Apr. 10-14, 2007, . pp. 1510-1516.
Parker et al. Advanced Imaging Catheter Gives Surgeons the Inside Picture; Brochure Jun. 12, 2013: https//www.llnl.gov/str/DaSilva.html.
Patterson et al. Time Resolved Reflectance and Transmittance for the Non-Invasive Measurement of Tissue Optical Properties; Applied Optics vol. 28, No. 12, Jun. 15, 1989 pp. 2331-2336.
Peracchia Surgical Education in the Third Millennium; Annuals of Surgery, vol. 234, No. 6. 2001. pp. 709-712.
Pettit et al. Dynamic Optical Properties of Collagen-Based Tissue During ARF Excimer Laser Ablation; Applied Optics vol. 32, No. 4 Feb. 1, 1993, pp. 488-493.
Piers et al. A Micro Optical Force Sensor for Force Feedback During Minimally Invasive Robotic Surgery; Elsevier Sensors and Actuators A 115, 2004, pp. 447-455.
Polygerinos et al. MRI-Compatible Fiber-Optic Force Sensors for Catheterization Procedures; IEEE Sensors Journal vol. 10 No. 10, Oct. 2010, pp. 1598-1608.
Post et al.; Outcome After Complete Percutaneous Removal of Infected Pacemaker Systems and Implantable Cardiac Defibrillators; Internal Medicine Journal 36, 2006, pp. 790-792.
Prasad et al. A Modular 2-DOF Force-Sensing Instrument for Laparoscopic Surgery; MICCAI 2003, LNCS 2878 pp. 279-286.
Puangmali et al. State-Of-The Art in Force and Tactile Sensing for Minimally Invasive Surgery; IEEE Sensors Journal vol. 8, No. 4, Apr. 2008, pp. 371-381.
Rajan et al. Photonic Crystal Fiber Sensors for Minimally Invasive Surgical Devices; IEEE Transactions on Biomedical Engineering, vol. 59, No. 2, Feb. 2012, pp. 332-338.
Reiley et al. Review of Methods for Objective Surgical Skill Evaluation Surg Endosc, vol. 25, 2011 pp. 356-366.
Richards et al. Skills Evaluation in Minimally Invasive Surgery Using Force/Torque Signatures; Surg Endosc vol. 14, 2000, pp. 791-798.
Rinaldi et al. Determinants of Procedural Outcome of Chronically Implanted Pacemaker and Defibrillator Leads Using the Excimer Laser Sheath Heart.bmj.com, Dec. 5, 2012, 3 pages.
Rocha et al. Fluorescence and Reflectance Spectroscopy for Identification of Atherosclerosis in Human Carotid Arteries Using Principal Components Analysis; Photomedicine and Laser Surgery vol. 26, No. 4, 2008, pp. 329-335.
Rosen et al. Markov Modeling of Minimally Invasive Surgery Based on Tool/Tissue Interaction and Force/Torque Signatures for Evaluating Surgical Skills; IEEE Transactions on Biomedical Engineering, vol. 48, No. 5 May 2001, 13 pages.
Rovithakis Artificial Neural Networks for Discriminating Pathologic From Normal Peripheral Vascular Tissue; IEEE Transactions on Biomedical Engineering, vol. 48, No. 10, Oct. 2001 pp. 1088-1097.
Ruttmann et al. Transvenous Pacemaker Lead Removal Is Safe and Effective Even in Large Vegetations: An Analysis of 53 Cases of Pacemaker Lead Endocarditis; Pace vol. 26, Mar. 2006 pp. 231-236.
Sangpradit et al. Tissue Identification Using Inverse Finite Element Analysis of Rolling Indentation; 2009 IEEE International Conference on Robotics and Automation; Kobe, Japan, May 12, 17, 2009, 6 pages.
Schroeder et al. Visualizing Surgical Training Databases: Exploratory Visualization, Data Modeling, and Formative Feedback for Improving Skill Acquisition: IEEE Computer Graphics and Applications, 2011, 11 pages; DOI 10.1109/MCG.2012.67.
Seibold et al. Prototype of Instrument for Minimally Invasive Surgery With 6-Axis Force Sensing Capability ; Proceedings of the 2005 IEEE International Conference on Robotics and Automation, Apr. 2005, 6 pages.
Shah et al. Evaluation of a New Catheter Sensor for Real-Time Measurement of Tissue Contact; Heart Rhythm, vol. 3, No. 5, Supplement, May 2006 pp. S75-S76.
Simone et al. A Low Cost Instrumented Glove for Extended Monitoring and Functional Hand Assessment; Journal of Neuroscience Methods 160, 2007 pp. 335-348.
Smith et al. Extraction of Transvenous Pacing and ICD Leads; Pace vol. 31 Jun. 2008 pp. 736-752.
Sohail et al. Management and Outcome of Permanent Pacemaker and Implantable Cardioverter-Defibrillator Infections; Journal of the American College of Cardiology, vol. 49, No. 18, 2007 pp. 1851-1859.
Sokollik et al. New Model for Skills Assessment and Training Progress in Minimally Invasive Surgery; Surg Endosc vol. 18, 2004, pp. 495-500.
Sosa et al. The Importance of Surgeon Experience for Clinical and Economic Outcomes From Thyroidectomy; Annals of Surgery vol. 228, No. 3 pp. 320-330.
Spectranetics User Manual VisiSheath Dilator Sheath, 2011, 112 Pages.
Spectranetics X80 User Manual ELCA Coronary Laser Atherectomy Catheter. Mar. 2012, 16 pages.
SPI2006 Shear Sensor Brochure—Real-Time Surface Shear Sensing Application: Human Interface; Tactilus Technology, 2006, 1 page.
Sturman et al. A Survey of Glove-Based Input; Clumsy Intermediary Devices Constrain Our Interaction With Computers and Their Applications. Glove-Based Input Devices Let US Apply Our Manual Dexterity to the Task: IEEE Computer Graphics & Applications, Jan. 1994. pp. 30-39.
Sun et al. A Sub-Millemetric, 0.25 Mn Resolution Fully Integrated Fiber-Optic Force Sensing Tool for Retinal Microsurgery; Int J Comput Assist Radiol Surg. vol. 4(4): Jun. 2009, pp. 383-390.
Takano et al. Changes in Coronary Plaque Color and Morphology by Lipid-Lowering Therapy With Atorvastatin: Serial Evaluation by Coronary Angioscopy; The Journal of the American College of Cardiology, vol. 42, No. 4, 2003 pp. 680-686.
Taroni et al. In Vivo Absorption and Scattering Spectroscopy of Biological Tissues; Photochem. Photobiol. Sci. vol. 2, 2003. pp. 124-129.
Turchin et al. Novel Algorithm of Processing Optical Coherence Tomography Images for Differentiation of Biological Tissue Pathologies; Journal of Biomedical Optics 10(6), Nov./Dec. 2005, 11 pages.
Turner et al. Development and Testing of a Telemanipulation System With Arm and Hand Motion; Accepted to 2000 ASME IMECE Symp. Haptic Interfaces, 2000, 7 pages.
Valdastri et al. Integration of a Miniaturized Triaxial Force Sensor in a Minimally Invasive Surgical Tool; IEEE Transactions on Biomedical Engineering, vol. 53, No. 11, Nov. 2006 pp. 2397-2400.
Van der Meer et al. Quantitative Optical Coherence Tomography of Arterial Wall Components; Lasers in Medical Science vol. 20, 2005, pp. 45-51.

(56) References Cited

OTHER PUBLICATIONS

Van der Meijden et al. The Valve of Haptic Feedback in Conventional and Robot-Assisted Minimal Invasive Surgery and Virtual Reality Training: A Current Review; Surg. Endosc vol. 23, 2009. pp. 1180-1190.
Van Leeuwen et al. Origin of Arterial Wall Dissections Induced by Pulsed Excimer and Mid-Infrared Laser Ablation in the PIGL; JACC vol. 19, No. 7, Jun. 1992, pp. 1610-1618.
Van Lindert et al. The Influence of Surgical Experience on the Rate of Intraoperative Aneurysm Rupture and Its Impact on Aneurysm Treatment Outcome; Surg Neurol vol. 56, 2001, pp. 151-158.
Wagner et al. The Role of Force Feedback in Surgery: Analysis of Blunt Dissection; Presented at the Tenth Symposium on Haptic Interfaces for Virtual Environment and Teleoperator Systems, Mar. 24, 25, 2002, 7 pages.
Walker et al. Surgical Safety Checklists: Do They Improve Outcomes?; British Journal of Anaesthesia, 2012, pp. 1-8.
Wang et al. Characterization of a Silicon=Based Shear-Force Sensor on Human Subjects; IEEE Trans Biomed Eng., 2002 1 page.
Wang et al. Miniature All-Silica Optical Fiber Pressure Sensor With an Ultrathin Uniform Diaphragm; Optics Express vol. 18, No. 9, Apr. 26, 2010 pp. 9006-9014.
Wang et al. Review: The Physiological and Computational Approaches for Atherosclerosis Treatment; IJCA-15372, 2012, 13 pages.
Wang, Lin et al. "Characterization of a Silicon-Based Shear-Force Sensor on Human Subjects." IEEE Transactions on Biomedical Engineering, vol. 49, No. 11. Nov. 2002. pp. 1340-1347.
Wazni et al. Lead Extraction in the Contemporary Setting: The Lexicon Study; Journal of the American College of Cardiology vol. 55, No. 6, 2010, pp. 579-586.
Weiss et al. Muscular and Postural Synergies of the Human Hand; J. Neurophysiol 92, 2004pp. 523-535.
Wilkoff et al. Transvenous Lead Extraction: Heart Rhythm Society Expert Consensus on Facilities, Training, Indications, and Patient Management; Heart Rhythm, vol. 6, No. 7, Jul. 2009, pp. 1086-1104.
International Search Report and Written Opinion issued in PCT/2014/019258, mailed Aug. 8, 2014, 21 pages.
International Search Report and Written Opinion issued in PCT/2014/019283, mailed Jun. 20, 2014, 15 pages.
International Search Report and Written Opinion issued in PCT/2014019278, mailed May 7, 2014, 14 pages.
Abeysinghe et. al. A Novel MEMS Pressure Sensor Fabricated on an Optical Fiber; IEEE Photonics Technology Letters vol. 13. No. 9 Sep. 2001 pp. 993-995.
Agency for Healthcare Research and Quality Adjunctive Devices in PCI to Remove Thrombi or Protect Against Distal Embolization in Patients With ACS: A Clinician Research Summary; Effective Health Care Program; AHRQ Pub. No. 11 (12)-EHC089-3 May 2012 4 pages.
Arifler et. al. Light Scattering From Collagen Fiber Networks: Micro-Optical Properties of Normal and Neoplastic Stroma; Biophysical Journal vol. 92 May 2007, pp. 3260-3274.
Ashok et al. Raman Spectroscopy Sensor for Surgical Robotics-Instrumentation and Tissue Differentiation Algorithm Biomedical Optics and 3D Imaging OSA 2012 4 pages.
Bach et al., Design and Fabrication of 60-Gb/s InP-Based Monolithic Photoreceiver OEICs and Modules, IEEE Journal of Selected Topics in Quantum Electronics, vol. 8, No. 6, Nov. 1, 2002, 6 pgs.
Baddour et al. Update on Cardiovascular Implantation Electronic Device Infections and Their Management: A Scientific Statement From the American Heart Association Circulation 121: Jan. 2010, pp. 458-477.
Badr et al. The State of the Excimer Laser for Coronary Intervention in the Drug-Eluting Stent Era Cardiovascular Revascularization Medicine 14, 2013, pp. 93-98.
Bann et al. Attitudes Towards Skills Examinations for Basic Surgical Trainees J. Clin Pract Jan. 2005, 59, 1. pp. 107-113.

Baztarrica et al. Transvenous Extraction of Pacemaker Leads in Infective Endocarditis With Vegetations ≥20MM: Our Experience; Clinl. Cardiol 35, 4, 2012 pp. 244-249.
Beauvoit et al. Contribution of the Mitochondrial Compartment to the Optical Properties of the Rat Liver: A Theoretical and Practical Approach Biophysical Journal vol. 67 Dec. 1994 pp. 2501-2510.
Beccai et al. Design and Fabrication of a Hybrid Silicon Three-Axial Force Sensor for Biomechanical Applications; Sensors and Actuators A 120, 2005, pp. 370-382.
Berkelman et al. A Miniature Microsurgical Instrument Tip Force Sensor for Enhanced Force Feedback During Robot-Assisted Manipulation; IEEE Transactions on Robotics and Automaton, vol. 19, No. 5, Oct. 2003, pp. 917-922.
Bilodeau et al. Novel Use of a High-Energy Excimer Laser Catheter for Calcified and Complex Coronary Artery Lesions Catheterization and Cardiovascular Interventions 62: 2004 pp. 155-161.
Bindig et al. Fiber-Optical and Microscopic Detection of Malignant Tissue by Use of Infrared Spectrometry Journal of Biomedical Optics vol. 7 No. 1 Jan. 2002 pp. 100-108.
Bishop et al. Paid Malpractice Claims for Adverse Events in Inpatient and Outpatient Settings; JAMA vol. 205 No. 23 Jun. 15, 2011, pp. 2427-2431.
Bittl et al. Meta-Analysis of Randomized Trials of Percutaneous Transluminal Coronary Angioplasty Versus Atherectomy, Cutting Balloon Atherotomy, or Laser Angioplasty Journal of the American College of Cardiology vol. 43 No. 6 2004 pp. 936-942.
Bongiomi et al. Transvenous Removal of Pacing and Implantable Cardiac Defibrillating Leads Using Single Sheath Mechanical Dilatation and Multiple Venous Approaches; High Success Rate and Safety in More Than 200 Leads; European Heart Journal vol. 29, 2008, pp. 2886-2893.
Bracke et al. Pacemaker Lead Complications: When Is Extraction Appropriate and What Can We Learn From Published Data? Heart 2001 vol. 85 pp. 254-259.
Brennan et al. Analysis of Errors Reported by Surgeons At Three Teaching Hospitals, Surgery vol. 3, No. 6, 2003 pp. 614-621.
Britton Chance Optical Method; Annu Rev. Biophys. Chem vol. 20 1991 pp. 1-30.
Buch et al. Pacemaker and Defibrillator Lead Extraction; Circulation 2011:123 pp. 378-380.
Byrd et al. Clinical Study of the Laser Sheath for Lead Extraction: The Total Experience in the United States; Journal of Pacing and Clinical Electrophysiology, vol. 25 No. 5, May 2002 pp. 804-808.
Byrd et al. Intravascular Lead Extraction Using Locking Stylets and Sheaths; Pace vol. 13 Dec. 1990, pp. 1871-1875.
Candefjord et al. Combining Fibre Optic Raman Spectroscopy and Tactile Resonance Measurement for Tissue Characterization; Meas. Sci Technol. vol. 21, 2010 125801 8 pages.
Candinas et al. Postmortem Analysis of Encapsulation Around Long-Term Ventricular Endocardial Pacing Leads; Mayo Clin Proc. vol. 74, Feb. 1999, pp. 120-125.
Carlson et al. Motion Capture Measures Variability in Laryngoscopic Movement During Endotracheal Intubation: A Preliminary Report; 2012 Society for Simulation in Healthcare, vol. 7, No. 1, Aug. 2012 pp. 255-260.
Chan et al. Effects of Compression on Soft Tissue Optical Properties; IEEE Journal of Selected Topics in Quantum Electronics, vol. 2 No. 4, Dec. 1996 pp. 943-950.
Cheong et al. A Review of the Optical Properties of Biological Tissues; IEEE Journal of Quantum Electronics vol. 26, No. 12, Dec. 1990 pp. 2166-2185.
Chung et al. Advanced Fibre Bragg Grating and Microfibre Bragg Grating Fabrication Techniques; A Thesis Submitted in Partial Fulfillment of the Requirements for the Degree of Doctor of Philosophy the Hong Kong Polytechnic University; Mar. 2012; 130 pages.
Cruz et al. Internal Mammary Arterial Injury From Lead Extraction: A Clinically Subtle Yet Important Complication of Implantable Device Removal; Cardiology Research and Practice vol. 2011, Article ID 408640, (2011) 5 pages.
Da et al. Overview of the Vascular Interventional Robot; The International Journal of Medical Robotics and computer assisted surgery 2008;4: pp. 289-294.

(56) References Cited

OTHER PUBLICATIONS

Dallon et al. A Mathematical Model for Spatially Varying Extracellular Matrix Alignment; SIAM J. Appl. Math. vol. 61, No. 2, 2000, pp. 506-527.
Deharo et al. Pathways for Training and Accreditation for Transvenous Lead Extraction: A European Heart Rhythm Association Position Paper; Europace 14 (2012) pp. 124-134.
Dipietro et al. Evaluaton of an Instrumented Glove for Hand-Movement Acquisition; Journal of Rehabilitation Research and Development vol. 40, No. 2, Mar./Apr. 2003, pp. 179-190.
Eichhorn et al. Carbon Nanotube Filled Composite Material Analysis Utilizing Nano and Conventional Testing Techniques; NIP & Digital Fabrication Conference, 2010 International Conference on Digital Printing Technologies. 5 Pages.
Eichhorn et al. Flexible Carbon Nanotube Composite Sensors for Medical Device Application; J. Med. Devices 7(2), 020943 (Jun. 11, 2013) (2 pages)Paper No. MED-13-1050; doi: 10.1115/1.4024311.
ELCA Coronary Laser Atherectomy Catheter Brochure, Spectranetics, 2012.
El-Sawah et al. A Prototype for 3-D Hand Tracking and Posture Estimation; IEEE Transactions on Instrumentation and Measurement, vol. 57, No. 8, Aug. 2008, pp. 1627-1636.
Endo et al. Clinical Utility of Intraprocedural Transesophagael Echocardiography During Transvenous Lead Extraction; Journal of the American Society of Echocardiography vol. 21 No. 7, Jul. 2008 pp. 862-867.
Epstein et al. Gross and Microscopic Pathological Changes Associated With Nonthoracotomy Implantable Defibrillator Lead; Circulation 1998:98: 1517-1524.
Erturk et al. Outcome of Surgery for Acromegaly Performed by Different Surgeons: Importance of Surgical Experience; Pituitary 8: 2005, pp. 93-97.
Esposito et al. Morphologic and Immunohistochemical Observations of Tissues Surrounding Retrieved Transvenous Pacemaker Leads; Wiley Periodicals, Inc. 2002, pp. 548-558.
Faber et al. Light Absorption of (Oxy-) Hemoglobin Assessed by Spectroscopic Optical Coherence Tomography; Optics Letters vol. 28, No. 16, Aug. 15, 2003 pp. 1436-1438.
Fanson et al. A System for Laparoscopic Surgery Ergonomics and Skills Evaluation; Journal of Endourology vol. 25, No. 7, Jul. 2011 pp. 1111-1114.
Fung et al. A PMMA-Based Micro Pressure Sensor Chip Using Carbon Nanotubes As Sensing Elements; IEEE International Conference on Micro Electro Mechanical Systems, vol. 18, 2005 pp. 251-254.
Ghosh et al. Laser Lead Extraction: Is There a Learning Curve?; Pace, vol. 28; Mar. 2005 pp. 180-184.
Golzio et al. Prevention and Treatment of Lead Extraction Complications; Transvenous Lead Extraction; Springer-Verlag Italia 2011 pp. 129-136.
Wise et al. Evaluation of a Fiber Optic Glove for Semi-Automated Goniometric Measurements; Journal of Rehabilitation Research and Development vol. 27 No. 4, 1990, pp. 411-424.
Wollmann et al. Two Different Therapeutic Strategies in ICD Lead Defects: Additional Combined Lead Versus Replacement of the Lead; Journal of Cardiovascular Electrophysiology vol. 18, No. 11, Nov. 2007, pp. 1172-1177.
Yamamoto et al. Tissue Property Estimation and Graphical Display for Teleoperated Robot-Assisted Surgery; 2009 IEEE International Conference on Robotics and Automation, May 12, 17, 2009, 7 pages.
Yokoyama et al. Novel Contact Force Sensor Incorporated in Irrigated Radiofrequency Ablation Catheter Predicts Lesion Size and Incidence of Steam Pop and Thrombus Clinical Perspective; Circulation Arrhythmia and electrophysiology: Journal of the American Heart Association, Dec. 2008, pp. 353-362.
Yun et al. An Instrumented Glove for Grasp Specification in Virtual-Reality-Based Point and Direct Telerobotics; IEEE Transactions on Systems, Man, and Cybernetics—Bart B: Cybernetics, vol. 27, No. 5, Oct. 1997, pp. 835-846.
Zhan et al. Excess Length of Stay, Charges, and Mortality Attributable to Medical Injuries During Hospitalization; Journal of American Medical Association, vol. 290, No. 14, Oct. 8, 2003, pp. 1868-1874.
Advisory Action for U.S. Appl. No. 12/337,232 mailed Aug. 8, 2013, 3 pages.
U.S. Appl. No. 14/586,543, filed Dec. 30, 2014.
European Search Report issued in EP Application No. 05796879.4 mailed Mar. 6, 2008, 7 pages.
European Search Report issued in EP Application No. 08010688.3. mailed Feb. 17, 2009, 6 pages.
Final Official Action for U.S. Appl. No. 12/337,232 mailed Apr. 23, 2013, 11 pages.
Grundfest, Warren S., MD, et al., "Laser Ablation of Human Atherosclerotic Plaque Without Adjacent Tissue Injury," JACC vol. 5, No. 4, (Apr. 1985), pp. 929-933.
International Preliminary Report on Patentability issued in PCT/US2009/066133, mailed Jun. 21, 2011, 8 pages.
International Search Report and Written Opinion issued in PCT/US2005/033029, mailed Oct. 3, 2006, 1 page.
International Search Report and Written Opinion issued in PCT/US2009/066133, mailed Jan. 26, 2010, 8 pages.
Notice of Allowance for U.S. Appl. No. 12/649,759 mailed May 16, 2013, 12 pages.
Notice of Allowance for U.S. Appl. No. 11/228,845 mailed Jun. 5, 2009, 8 pages.
Notice of Allowance for U.S. Appl. No. 12/406,807 mailed Aug. 2, 2010, 7 pages.
Notice of Alowance for U.S. Appl. No. 12/337,232 mailed Sep. 6, 2013, 11 pages.
Official Action for U.S. Appl. No. 11/228,845 mailed Jan. 12, 2009, 13 pages.
Official Action for U.S. Appl. No. 11/228,845 mailed Sep. 3, 2008, 10 pages.
Official Action for U.S. Appl. No. 12/337,232 mailed Mar. 23, 2012, 9 pages.
Official Action for U.S. Appl. No. 12/337,232 mailed Sep. 13, 2012, 10 pages.
Official Action for U.S. Appl. No. 12/649,759 mailed Aug. 30, 2012, 11 pages.
Official Action for U.S. Appl. No. 12/649,759 mailed Jul. 16, 2012, 9 pages. (Restriction Requirement).
U.S. Appl. No. 14/586,312, filed Dec. 30, 2014.
U.S. Appl. No. 14/586,529, filed Dec. 30, 2014.
Kahol, K. et al. Effect of Fatigue on Psychomotor and Cognitive Skills. The American Journal of Surgery: Association for Surgical Education, 195:195-204, 2008.
Esenaliev, O. R., et al. Laser Ablation of Atherosclerotic Blood Vessel Tissue Under Various Irradiation Conditions. IEEE Transactions on Biomedical Engineering, 36(12):1188-1194, Dec. 1989.
Spectranetics. ELCA Coronary Laser Atherectomy Catheter: Instructions for Use, 0.9 mm OTW and 0.9 mm RX X-80 Catheter Models, Mar. 14, 2012, pp. 1-16.
Wikipedia, Linear discriminant analysis, Dec. 21, 2013, http://en.wikipedia.org/wiki/Linear_discriminant_analysis.
Sensor-Response-Compressive Force versus CNT sensor readout Chart, 2 pages, available May 23, 2013.
Interlink Electronics. State-of-the-Art Pointing Solutions for the OEM—FSR Force Sensing Resistor Integration Guide and Evaluation Parts Catalog: 400 Series Evaluation Parts With Suggested Electrical Interfaces. Interlink Electronics, Version 1.0 (90-45632 Rev. D), Camarillo, CA, pp. 1-26, available 2002.
Extended European Search Report issued in European Patent Application 14773432.1, mailed Oct. 4, 2016, 6 pages.

\* cited by examiner

INTELLIGENT CATHETER

FIELD

The disclosure relates generally to endovascular devices and particularly to monitoring the use of catheters.

BACKGROUND

Catheters are medical devices that can be inserted into a body cavity, duct, or vessel to treat diseases or perform a surgical procedure. Catheterization, for example, is performed in cardiovascular, urological, gastrointestinal, neurovascular, and ophthalmic applications. Catheters can allow drainage, administration of fluids or gases, access by surgical instruments, and perform wide variety of other tasks depending on the type of catheter. Catheters can, for instance, include energy emitting devices, such as laser and other radiation emitters, to ablate or cauterize tissue, particularly in coronary catheterization and lead removal. In most uses, catheter is a thin, flexible tube ("soft" catheter) though catheters are available in varying levels of stiffness depending on the application.

In energized catheters, such as laser catheters, it can be important to identify the catheter to an energizing base unit, such as an excimer laser system, for purposes of selecting appropriate specifications, requirements, and other operating information (such as active area, maximum and minimum allowable fluence, and repetition rate (e.g., lasing on/off time), and lasing train time) required for catheter energization. One method of identifying the catheter to the energizing base unit is to use a sequence of pins mounted to a proximal coupler of the catheter. The pin arrangement or sequence actuates switches in the catheter's coupler to generate a signal, which is forwarded to the microcontroller of the energizing base unit. Using a lookup table and the signal, the microcontroller can identify the type and/or model of the catheter and therefore the appropriate catheter specifications, requirements, and other operating information. Each type and/or model of catheter has a unique pin sequence to actuate different switches for generating different signals.

The arrangement can create problems.

First, the operating information is typically contained in firmware. When new catheters are introduced that do not correspond to the operating information already programmed in firmware, a new microcontroller must be installed containing updated code along with the operating information to operate the catheter. This can require expensive and time-consuming base unit upgrades.

Second, many catheters are disposable devices for patient health and safety. The arrangement enables unscrupulous health care providers to reuse catheters for different patients, thereby increasing the risk of infection and disease transmission Third, one catheter manufacturer can duplicate the pin sequence of a different catheter manufacturer and thereby use the other catheter manufacturer's base unit. This situation is unsafe. The catheter manufacturer duplicating the pin sequence does not know the operating information in the base unit's firmware, thereby potentially causing the duplicated catheter to be operated using improper and unsafe operating information.

SUMMARY

These and other needs are addressed by the various aspects, embodiments, and/or configurations of the present disclosure. The disclosure is directed generally to an endovascular device monitoring and/or control system.

A method, according to the disclosure, can include the steps of:

(a) receiving, by a microprocessor executable verification module in a base unit configured to couple to an endovascular device, an identifier of the endovascular device from a memory of the endovascular device; and (b) based on the identifier, one or more of configuring, by the verification module, the endovascular device for use and determining, by the verification module, whether the endovascular device can be enabled for use.

A system, according to the disclosure, can include:

(a) a microprocessor executable verification module in a base unit configured to couple to an endovascular device and (b) a microprocessor readable identifier of the endovascular device in a memory of the endovascular device.

The base unit couples to the endovascular device, and the microprocessor executable verification module, based on the identifier, one or more of configures the endovascular device for use and/or determines whether the endovascular device can be enabled for use.

The identifier can be provided to the verification module wirelessly and/or by a wired connection. For example, the identifier can be provided wirelessly and be unrelated to a configuration of a connector of the catheter to a coupler of the base unit.

In accordance with this disclosure, a tangible and non-transient computer readable medium in a base unit, configured to couple to an endovascular device, can include microprocessor readable and executable instructions that, when executed, access the identifier of the endovascular device and, based on the identifier, can one or more of configure the endovascular device for use and/or determine whether the endovascular device can be enabled for use.

When the verification module, based on the identifier, configures the endovascular device for use, the verification module can use the identifier to determine an appropriate set of operating information for the endovascular device.

The operating information can be stored in the memory of the endovascular device.

The endovascular device can be a laser catheter. In that event, the operating information can include one or more of a physical dimension of the catheter, an active area, a maximum allowable fluence, a minimum allowable fluence, a repetition rate, and a lasing train time.

The verification module can use the identifier to determine whether the endovascular device can be enabled for use and, when the identifier cannot be enabled for use, disable, block, or otherwise prohibit the base unit from energizing the catheter.

The identifier can be unique the corresponding endovascular device.

The identifier can be common to a first plurality of endovascular devices but different than an identifier associated with a second plurality of endovascular devices.

The endovascular device can include in memory not only the identifier but also one or more of a use indicator, set of use restrictions, patient information, and operating information.

The memory of the endovascular device can be configured as a radio frequency identification tag, and the base unit can further include a radio frequency identification tag reader.

The present disclosure can provide a number of advantages depending on the particular aspect, embodiment, and/or configuration. The operating information can be contained not in base unit firmware but in readable and/or writable memory of the endovascular device itself. This can simplify tremendously the introduction and/or upgrade of endovascular devices. No area table can be required in software because that (and other) information is contained in the endovascular device's labeling. Second, the identifier can prevent effectively reuse of endovascular devices among multiple patients, making the devices truly disposable. For example, the identifier, such as a serial or model number, can be maintained in a non-volatile memory location and compared by the verification module to the identifier of newly inserted devices. When the same identifier is read a second time, the base unit may not allow endovascular device energization. This can provide substantial benefits for patient health and safety. Unscrupulous health care providers can no longer reuse catheters for different patients. Finally, the identifier can prevent one manufacturer from providing off-specification endovascular devices for a different manufacturer's base unit.

These and other advantages will be apparent from the disclosure.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

A "catheter" is a tube that can be inserted into a body cavity, duct, lumen, or vessel. In most uses, a catheter is a thin, flexible tube ("soft" catheter), though in some uses, it is a larger, solid ("hard") catheter.

The term "computer-readable medium" as used herein refers to any storage and/or transmission medium that participate in providing instructions to a processor for execution. Such a medium is commonly tangible and non-transient and can take many forms, including but not limited to, non-volatile media, volatile media, and transmission media and includes without limitation random access memory ("RAM"), read only memory ("ROM"), and the like. Non-volatile media includes, for example, NVRAM, or magnetic or optical disks. Volatile media includes dynamic memory, such as main memory. Common forms of computer-readable media include, for example, a floppy disk (including without limitation a Bernoulli cartridge, ZIP drive, and JAZ drive), a flexible disk, hard disk, magnetic tape or cassettes, or any other magnetic medium, magneto-optical medium, a digital video disk (such as CD-ROM), any other optical medium, punch cards, paper tape, any other physical medium with patterns of holes, a RAM, a PROM, and EPROM, a FLASH-EPROM, a solid state medium like a memory card, any other memory chip or cartridge, a carrier wave as described hereinafter, or any other medium from which a computer can read. A digital file attachment to e-mail or other self-contained information archive or set of archives is considered a distribution medium equivalent to a tangible storage medium. When the computer-readable media is configured as a database, it is to be understood that the database may be any type of database, such as relational, hierarchical, object-oriented, and/or the like. Accordingly, the disclosure is considered to include a tangible storage medium or distribution medium and prior art-recognized equivalents and successor media, in which the software implementations of the present disclosure are stored. Computer-readable storage medium commonly excludes transient storage media, particularly electrical, magnetic, electromagnetic, optical, magneto-optical signals.

"Coronary catheterization" is a generally minimally invasive procedure to access the coronary circulation and/or blood filled chambers of the heart using a catheter. It is performed for both diagnostic and interventional (treatment) purposes.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The terms "determine", "calculate" and "compute," and variations thereof, as used herein, are used interchangeably and include any type of methodology, process, mathematical operation or technique.

"Electromagnetic radiation" or "EM radiation" or "EMR" is a form of energy emitted and absorbed by charged particles which exhibits wave-like behavior as it travels through space. EMR has both electric and magnetic field components, which stand in a fixed ratio of intensity to each other, and which oscillate in phase perpendicular to each other and perpendicular to the direction of energy and wave propagation. The electromagnetic spectrum, in order of increasing frequency and decreasing wavelength, consists of radio waves, microwaves, infrared radiation, visible light, ultraviolet radiation, X-rays and gamma rays.

A "lead" is a conductive structure, typically an electrically insulated coiled wire. The electrically conductive material can be any conductive material, with metals and intermetallic alloys common. The outer sheath of insulative material is biocompatible and biostable (e.g., non-dissolving in the body) and generally includes organic materials such as polyurethane and polyimide. Lead types include, by way of non-limiting example, epicardial and endocardial leads. Leads are commonly implanted into a body percutaneously or surgically.

The term "means" as used herein shall be given its broadest possible interpretation in accordance with 35 U.S.C., Section 112, Paragraph 6. Accordingly, a claim incorporating the term "means" shall cover all structures, materials, or acts set forth herein, and all of the equivalents thereof. Further, the structures, materials or acts and the equivalents thereof shall include all those described in the summary of the invention, brief description of the drawings, detailed description, abstract, and claims themselves.

The term "module" as used herein refers to any known or later developed hardware, software, firmware, artificial intelligence, fuzzy logic, or combination of hardware and software that is capable of performing the functionality associated with that element. Also, while the disclosure is presented in terms of exemplary embodiments, it should be appreciated that individual aspects of the disclosure can be separately claimed.

"Radio-Frequency IDentification" (RFID) refers to the use of a wireless non-contact system that uses radio-frequency electromagnetic fields to transfer data from a tag attached to an object, for the purposes of automatic identification and/or tracking. Some tags require no battery and are powered and read at short ranges via magnetic fields (electromagnetic induction) (known as passive RFID tags). Others use a local power source and emit radio waves (electromagnetic radiation at radio frequencies) (known as active RFID tags). The tag contains electronically stored information which may be read from up to several meters away. Unlike a bar code, the tag does not need to be within line of sight of the reader and may be embedded in the tracked object.

A "surgical implant" is a medical device manufactured to replace a missing biological structure, support, stimulate, or treat a damaged biological structure, or enhance, stimulate, or treat an existing biological structure. Medical implants are man-made devices, in contrast to a transplant, which is a transplanted biomedical tissue. In some cases implants contain electronics, including, without limitation, artificial pacemaker, defibrillator, electrodes, and cochlear implants. Some implants are bioactive, including, without limitation, subcutaneous drug delivery devices in the form of implantable pills or drug-eluting stents.

The preceding is a simplified summary of the disclosure to provide an understanding of some aspects of the disclosure. This summary is neither an extensive nor exhaustive overview of the disclosure and its various aspects, embodiments, and/or configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and/or configurations of the disclosure are possible utilizing, alone or in combination, one or more of the features set forth above or described in detail below.

DETAILED DESCRIPTION

Endovascular device usage is monitored and/or controlled by an endovascular device verification module. While the endovascular device verification module is discussed with specific reference to energized catheters, it is to be understood that it can apply equally to other, typically powered or energized, endovascular devices, such as lead removal or extraction sheaths, needles, surgical instruments, snares, and the like. The endovascular device verification module can be used for any type of catheter, whether or not energized, including without limitation laser ablation, cauterization, and lead removal catheter systems.

Figure 1:
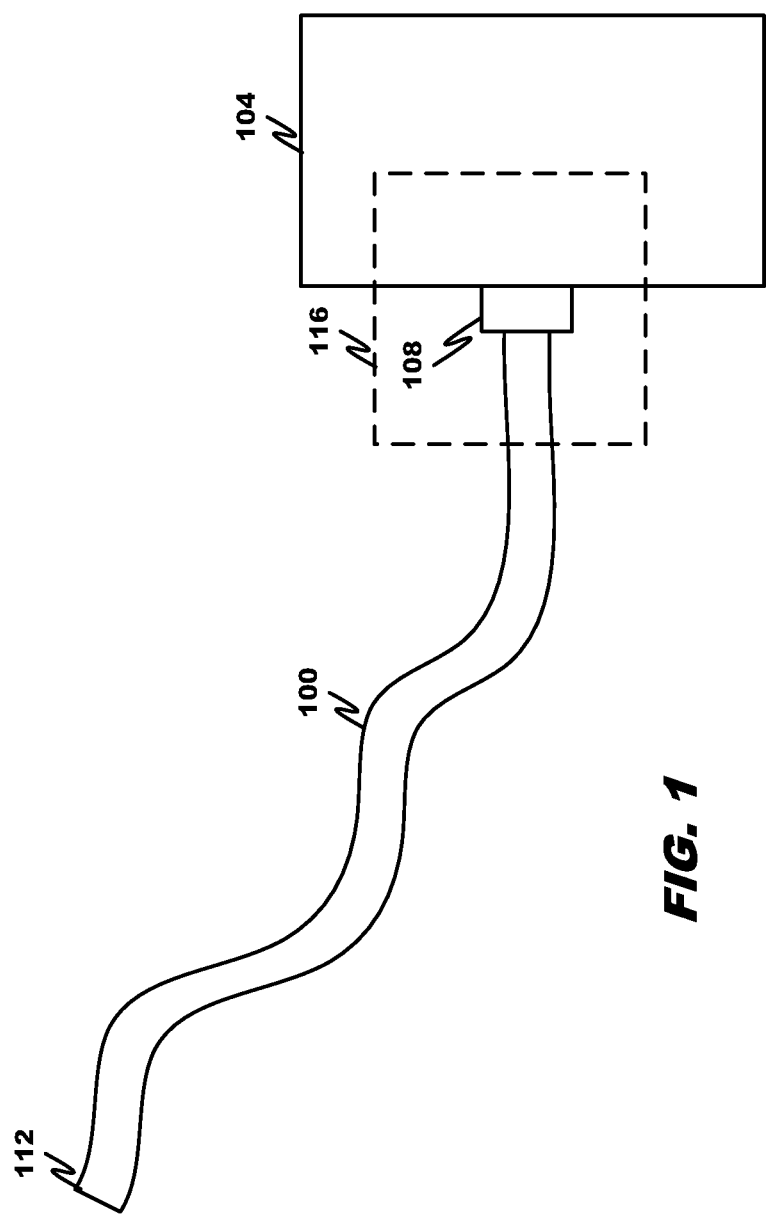
FIG. 1 depicts a catheter connected to an energizing base unit.

FIG. 1 depicts an energized catheter 100 coupled, at its proximal end, to an energizing base unit 104 (such as an excimer laser) via a coupler 108. A distal end 112 of the catheter 100 is used for endovascular procedures, such as lead removal, coronary catheterization and other applications requiring tissue ablation, separation, and/or removal. The energizing base unit 104 powers the energized catheter 100.

Figure 2:
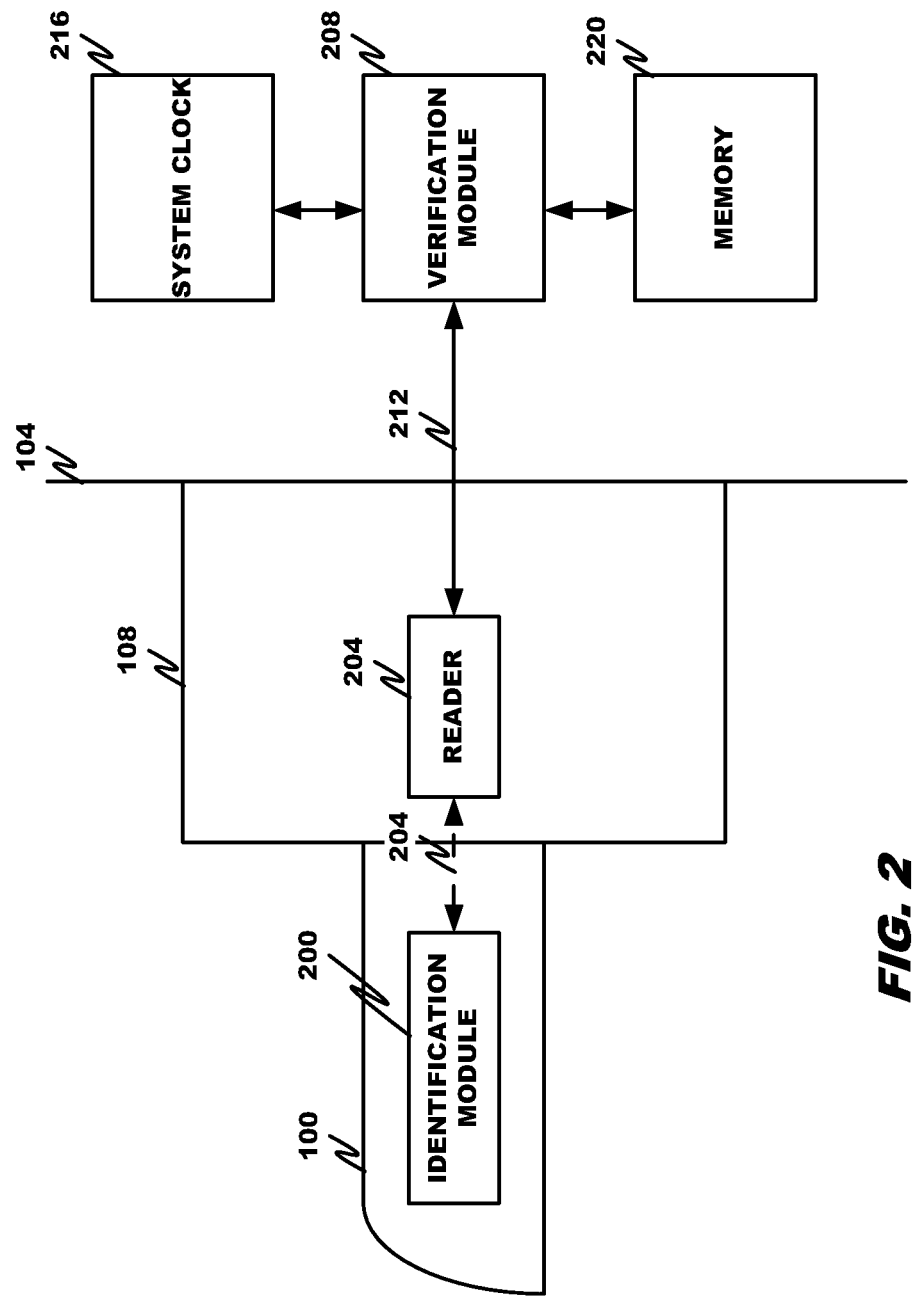
FIG. 2 is an exploded view of part of FIG. 1.

FIG. 2 is an exploded view of box 116 of FIG. 1. The proximal end of the catheter 100 includes an identification module 200 in wireless and/or wireline communication via link 204 with a reader 204 positioned in the coupler 108. A verification module 208 in the base unit 104 is in wireless or wired or wireline communication with a system clock 216 and memory 220 and, via link 212, with the reader 204.

Figure 8:
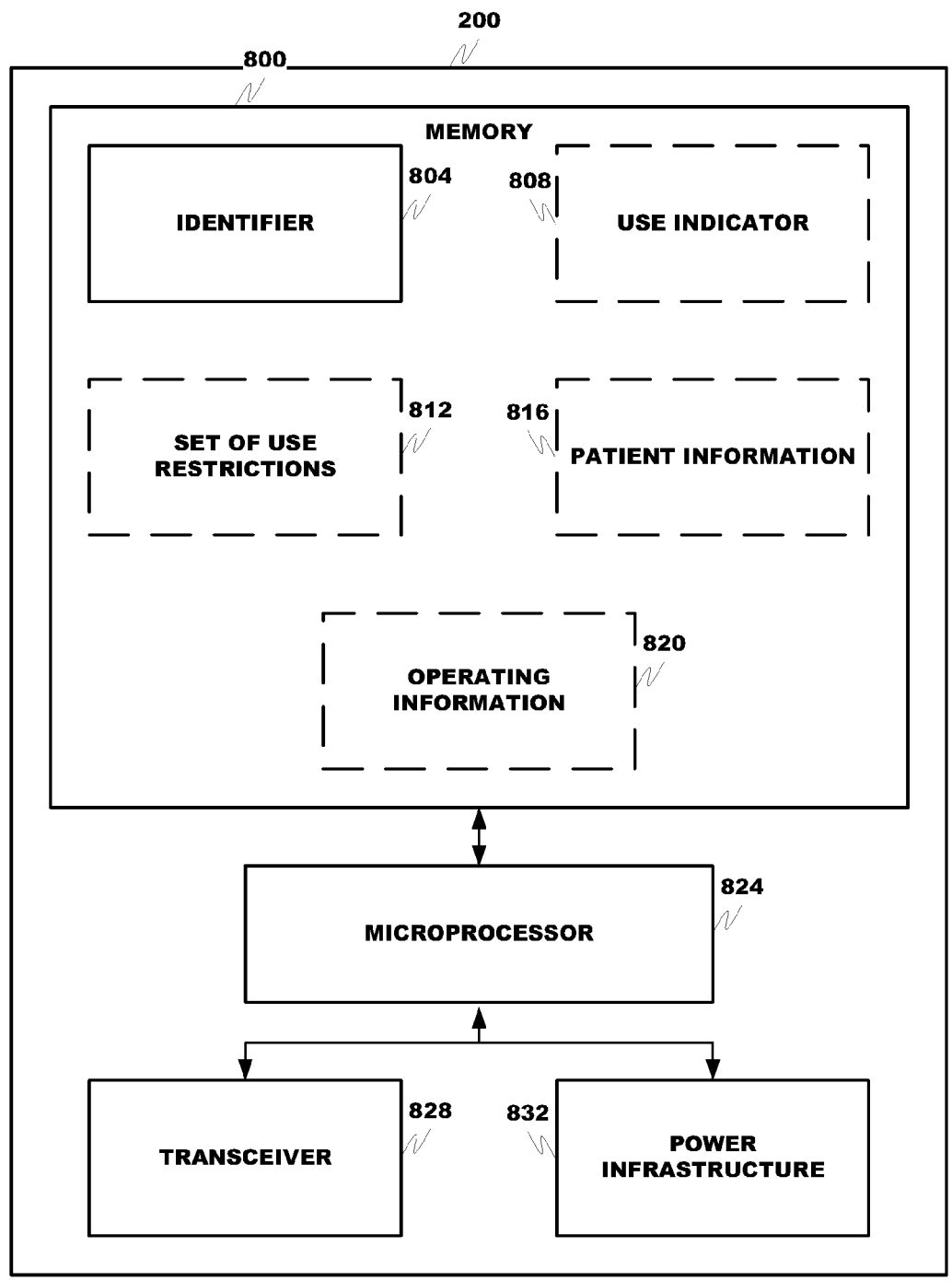
FIG. 8 depicts an identification module according to an embodiment.

With reference to FIG. 8, the identification module 200 comprises a memory 800, microprocessor 824, receiver, transmitter or transceiver 828, and, optionally, power infrastructure 832. The power infrastructure 832 can be an on board power supply or electrical components, such as an inductor, able to receive, by inductive coupling, electromagnetic energy to power the identification module 200.

The identification module 200 includes at least an identifier either unique to a single catheter (regardless of model number) (such that catheters of a common model number have different unique identifiers) or unique to a set of multiple catheters (having plural model numbers) (such that catheters of a common model number have common substantially unique identifiers). The use of an identifier unique to a single catheter (with each catheter having a unique serial number) can enable tracking of the catheter for statistical and control purposes. As an example of the latter configuration, catheters of a common model number would have a common identifier that is different from an identifier used for catheters of a different model number. The use of an identifier unique to a set of multiple catheters, while not allowing tracking, can facilitate and automate catheter set up and enable use of the correct operating parameters during catheter operation.

With reference to FIG. 8, the identification module 200 can include, in memory 800, not only identifier 804 but also one or more of a use indicator 808, set of use restrictions 812, patient information 816, and operating information 820. One or more of these items may also be included in the memory 220 of the base unit 104.

The use indicator 808 can take many different forms but generally indicates whether the catheter is eligible for use in a current procedure. In one configuration, each use indicator describes one or more historic event(s). As a first example, a catheter may be reused only for a selected patient but not for other patients. In that example, the use indicator 808 is a counter that defines a current number of uses for the identified patient. As a second example, the length of time that a catheter can be used is limited, and the use indicator 808 defines a current elapsed time period of use of the catheter. By way of illustration, the same catheter may be used on the same patient for a prolonged period as part of the same medical procedure. This usage may be involve repeated removal and reinsertion cycles. The use limitation could enable usage of the catheter for a limited period of time, such as 24 hours, regardless of the number of removal and reinsertion cycles. As a third example, the catheter is to be used in only one procedure, and the use indicator 808 is a bit that indicates whether the catheter has been used in a completed procedure. When the catheter has been used in a completed procedure the bit is set or unset, with the opposite bit setting indicating that the catheter has not yet been used in a completed procedure. As a further example, the use indicator 808 can contain detailed information about the usage history of the catheter, such as one or more start and stop timestamps for each energization cycle of the catheter, a description of how the catheter had been used, timing information describing how long the catheter had been used, and other relevant usage information which can be acted upon during subsequent reuse.

The set of use restrictions 812 define a set of restrictions on use imposed, by the manufacturer and/or health care provider, on the catheter. As examples, a use restriction can stipulate that the corresponding catheter can be used only for a certain type of procedure, that the catheter can be used only for a specified period or interval of time, that the catheter may not be used on more than one patient, and/or that the catheter can be used for a certain number of completed procedures for a selected patient. The use indicator 808 is updated either to describe instances of prior permissible use of the catheter and/or to indicate exhaustion of a use restriction and therefore ineligibility for further use.

Patient information 816 includes, for a selected patient currently being catheterized, the patient's name, age, weight, medical condition, medical procedure in which the catheter is being used, treating physician, health care provider, date(s) of catheter use, and the like.

The operating information 820 includes operating specifications, requirements, limitations, and other operating information for the corresponding catheter. Examples of operating information include physical dimensions of the catheter, active area, maximum and minimum allowable fluence, and repetition rate (e.g., lasing on/off time), lasing train time, and other attributes of the catheter.

The identification module 200 and memory 220 can be any computer readable medium, such as Programmable Read-Only Memory ("PROM"), Erasable Programmable Read-Only Memory or ("EPROM"), Electrically Erasable Programmable Read-Only Memory or ("EEPROM"), and flash memory and a processor (not shown).

The verification module 208 is microprocessor executable logic that determines whether use restrictions have been violated and updates data structures in the memory 220 and/or verification module 200 accordingly.

The reader 204 can be any device for accessing information in the identification module 200 and providing information update requests to the identification module 200 to update the use counter and other locally stored information.

Figure 3:
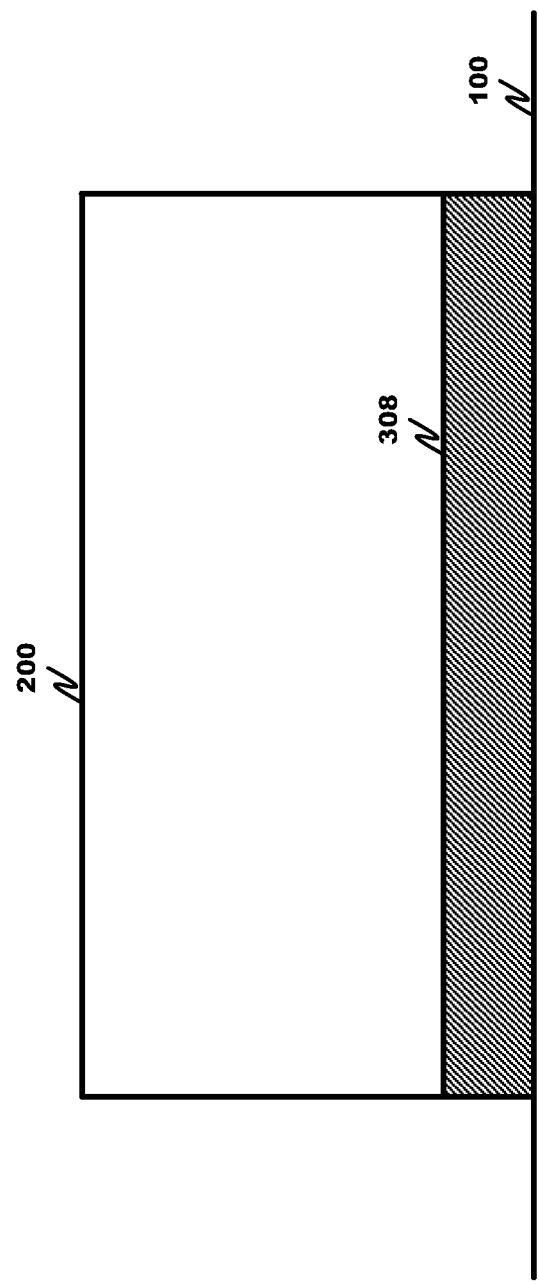
FIG. 3 depicts an identification module according to an embodiment.

In one application, the identification module 200 is configured as an active or passive RFID tag, and the reader 204 as an active or powered RFID reader. FIG. 3 depicts a design of a passive or active RFID tag suitable for use as the identification module 200. The identification module 200 is mounted on an RF adsorption material 308, which is in turn mounted on an interior or exterior surface of the catheter 100, with a proximal end of the catheter in proximity to the coupler 108 being preferred. Examples of RF and/or electromagnetic adsorption materials include organic polymeric materials (such as low density polyurethane impregnated with a dielectric lossy solution), and reticulated and dielectric foam absorbers. When the identification module 200 is mounted on an interior of the catheter, a EMR transparent and/or transmissive window may be positioned on the outer surface of the catheter over the identification module 200 to enable it to receive and transmit EMR signals wirelessly to the reader 204. The window generally has differing signal (EMR) transmission properties than the surrounding or adjacent catheter surface.

The operational modes of the identification module 200 and reader 204 will now be discussed with reference to FIGS. 4-5.

Figure 4:
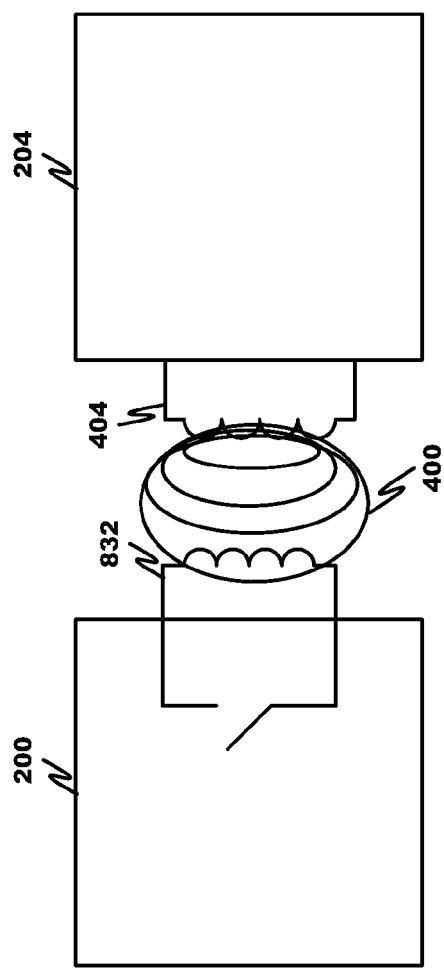
FIG. 4 depicts a mode of operating of the identification module and verification module.
Figure 5:
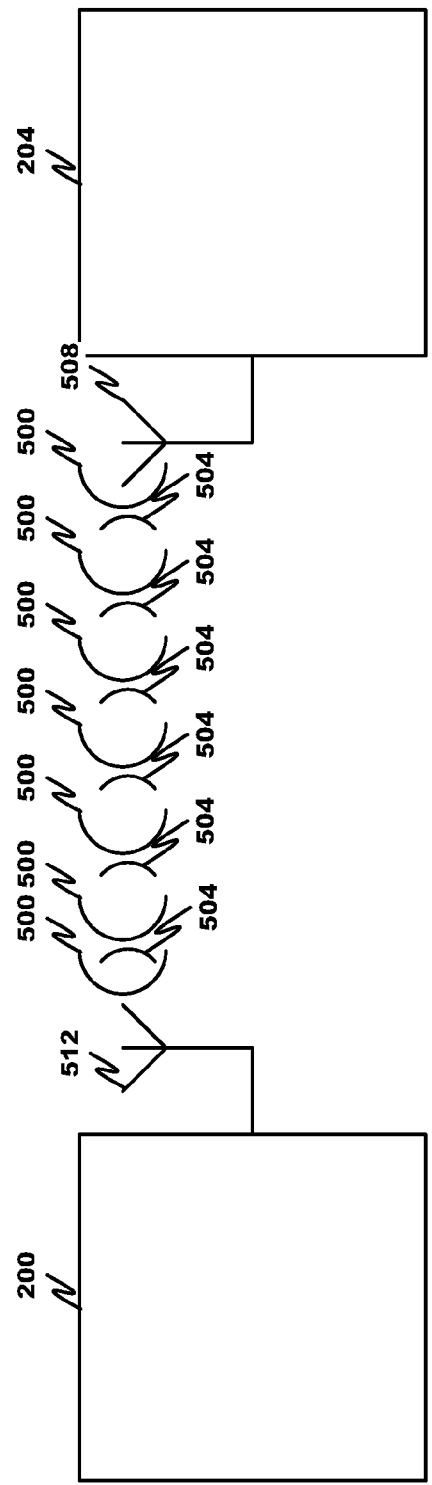
FIG. 5 depicts a mode of operating of the identification module and verification module.

Referring to FIG. 4, the identification module 200 can be configured as a passive RFID tag and the reader 204 as an active or powered RFID reader. As will be appreciated, passive RFID tags vary in how they communicate data to RFID readers and how they receive power from the RFID reader's inductive or electromagnetic field. This is commonly performed via two basic methods.

One method is known as load modulation and inductive coupling in the near field. In this method (shown in FIG. 4), the RFID reader 204 provides, by coupling infrastructure 404, a short-range alternating current magnetic field 400 that the passive RFID tag uses for both power and as a communication medium. Through a technique known as inductive (or near-field) coupling, the magnetic field 400 induces a voltage in the power infrastructure 832 (which is configured as an antenna coil) of the RFID tag 200, which in turn powers the tag. Each time the tag draws energy from the RFID reader's magnetic field, the RFID reader 204 itself can detect a corresponding voltage drop across its antenna leads. Capitalizing on this phenomenon, the tag 200 can communicate binary information to the reader 204 by switching ON and OFF a load resistor to perform load modulation. When the tag 200 performs load modulation, the RFID reader 204 detects this action as amplitude modulation of the signal voltage at the reader's antenna. Load modulation and inductive coupling can be found among passive RFID tags using frequencies from about 125 to 135 kHz and 13.56 MHz. Limitations that exist with regard to the use of such low frequencies include the necessity to use larger antennas, low data rate and bandwidth and a rather dramatic decay in the strength of the electromagnetic field ($1/r^6$), where r represents the distance between a low frequency interrogator and a passive RFID tag.

The other method is known as backscatter modulation and electromagnetic coupling in the far field. In this method (shown in FIG. 5), the RFID reader 204, by antenna 508, provides a medium-range electromagnetic field 500 that the passive RFID tag 200 uses for both power and a communication medium. Via a technique known as electromagnetic (or far-field) coupling, the passive RFID tag 200 draws energy from the electromagnetic field of the RFID reader 204. However, the energy contained in the incoming electromagnetic field is partially reflected back to the RFID reader 204 by the passive tag antenna 512. The precise characteristics of this reflection 504 depend on the load (resistance) connected to the antenna 512. The tag 200 varies the size of the load that is placed in parallel with the antenna 512 to apply amplitude modulation to the reflected electromagnetic waves, thereby enabling it to communicate information payloads back to the RFID reader 204 via backscatter modulation. Tags 200 using backscatter modulation and electromagnetic coupling typically provide longer range than inductively coupled tags and can be found most commonly among passive RFID tags operating at 868 MHz and higher frequencies. Far field coupled tags typically provide significantly longer range than inductively coupled tags, principally due to the much slower rate of attenuation (1/r2) associated with the electromagnetic far-field. Antennas used for tags employing far field coupling are typically smaller than their inductively coupled counterparts.

The identification module 200 can be configured as a semi-passive RFID tag and the reader 204 as an active or powered RFID reader. Semi-passive RFID tags can overcome two disadvantages of passive RFID tag designs, namely the lack of a continuous source of power for onboard telemetry and sensor asset monitoring circuits and range limitations. Semi-passive tags differ from passive tags in that they use an onboard battery as a power source to power communication and ancillary support circuits, such as temperature and shock monitoring. Although semi-passive tags employ an onboard power source, semi-passive RFID tags do not use the power source to directly generate RF electromagnetic energy. Rather, these tags typically make use of backscatter modulation and reflect electromagnetic energy from the RFID reader to generate a tag response similar to that of standard passive tags. The onboard battery is used only to provide power for telemetry and backscatter enabling circuits on the tag, not to generate RF energy directly.

The identification module 200 can be configured as an active RFID tag and the reader 204 as an active or powered RFID reader.

In some applications, the identifier is not contained in an identification module 200. In these applications, other approaches can be used to provide the identifier to the reader 204. By way of example, the identifier can be configured to reflect light in a detectable and consistent manner. The identifier typically has an optical property, such as reflectance (or reflectivity), absorbance (or absorption), and the like, different from that of the adjacent areas of the catheter body. The reader 204 is configured as a light source emits modulated or unmodulated light onto the catheter in proximity to the identifier. The reader 204 further includes an optical detector, such as an array of photoelectric devices, that capture light reflected by the identifier. The detector dissects the reflected light into its various spectra. The differing optical properties of the light reflected by the identifier when compared with the adjacent or surrounding catheter body are translated into an electric signal, which is output to the microprocessor executable verification module 208. An example of this type of identification module is a bar code representing the identifier. By way of further example, the identifier can be magnetic or have a magnetic property different from that of the adjacent or surrounding catheter body, with the magnetic elements being configured to represent the identifier. The reader 204 can be a magnetic field sensor, such as a rotating coil, Hall effect magnetometer, NMR magnetometer, SQUID magnetometer, or fluxgate magnetometer that can measure variations in magnetic field strength along a length of the catheter body and thereby read the identifier. The measured magnetic field variations when compared with the adjacent and/or surrounding catheter body are translated into an electric signal, which is output to the verification module 208. In yet another example, the identifier can have a different ultrasonic transmission property than the adjacent or surrounding catheter body, with the ultrasonic elements being configured to represent the identifier. The reader 204 is configured as an ultrasound transducer that acts both as the ultrasonic emitter and detector to detect reflected or transmitted ultrasonic energy and thereby read the identifier. An electrical signal is generated when the reader 204 reads the identifier, which signal is output to the verification module 208. In yet another example, the identifier includes a radiopaque material, such as gold or other metal, while the adjacent or surrounding catheter body includes a radiolucent material, or vice versa, such that the identifier has a different imaging property than the adjacent or surrounding catheter body, with the radiopaque or radiolucent elements, as the case may be, being configured to represent the identifier. The reader 204 emits one or more wavelengths of radiation (such as x-rays). An electrical signal is generated when the identifier passes the reader, which signal is output to the verification module 208. In a final example, the identifier has electrically conductive or have an electrical conductivity or resistivity different from that of the adjacent or surrounding catheter body, with the electrically conductive or conductive or resistive elements, as the case may be, being configured to represent the identifier. The reader 204 is configured to sense an electrical parameter, such as voltage, current, resistance, or ambient electric field to read the identifier. The reader 204, for example, can be a voltmeter, ammeter, magnetoresistive field sensor, Hall Effect current sensor transducer, potentiometer, oscilloscope, LCR meter, and the like. An electrical signal is generated when the identifier is read by the reader 204, which signal is output to the verification module 208.

An operation of the verification module 208 will now be discussed with reference to FIG. 6.

Figure 6:
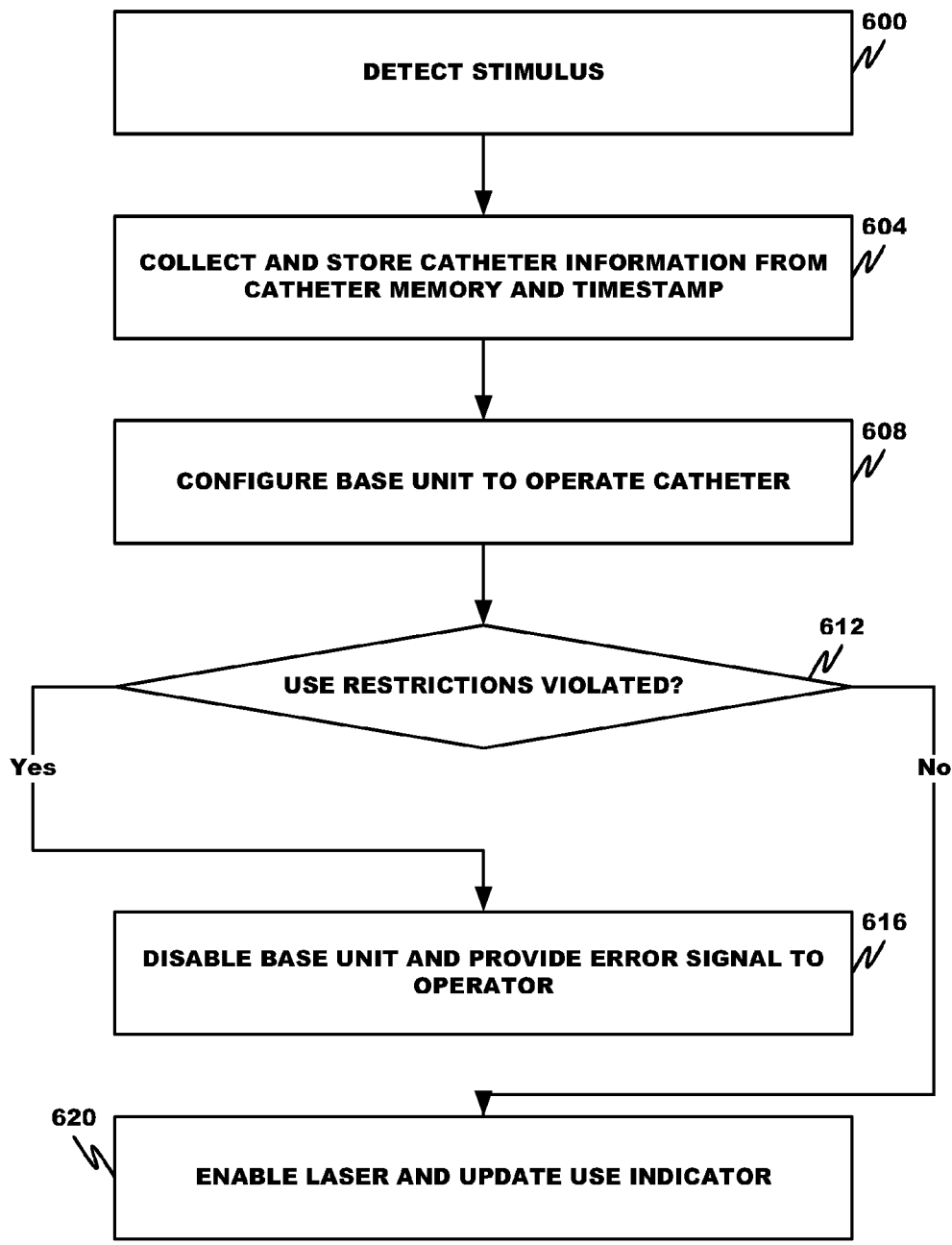
FIG. 6 depicts logic for the verification module according to an embodiment.

Referring to FIG. 6, the logic initiates, in step 600, when the verification module 208 detects a stimulus. The stimulus can, for example, be the passage of a selected period of time, realization of a specified clock setting, connection with a catheter, user input, and the like. For example, the stimulus can be the receipt by the verification module 208 of a notification signal from the coupler 108. This signal is generated by the coupler 108 immediately after it is connected to the catheter. Successful acknowledgement of the notification signal by the verification module 208 terminates notification signal transmission by the coupler 108.

In step 604, the reader 204 collects and forwards to the verification module 208 for storage in memory 220, catheter information from the catheter memory. The catheter information is stored in memory 220 with a corresponding timestamp from the system clock 216. The catheter information can include any of the information referenced previously. Upon detection of the stimulus, the reader 204 can periodically poll the identification module 200 for catheter information.

In step 608, the base unit is configured to energize the catheter. This can be done using operating information received from the identification module 200 and/or operating information retrieved from memory 220.

In decision diamond 612, the verification module 208 determines whether enabling the catheter would violate a use restriction. For example, the use indicator may indicate that further usage of the catheter is prohibited. By way of further example, the verification module 208 may need to compare the historic usage information associated with and/or contained within the use indicator against the set of usage restrictions to determine whether further usage of the catheter is permitted. In yet another example, the verification module 208 may compare the identifier with a listing of previously enabled identifiers and, when a match exists, conclude that use of the catheter would violate a use restriction.

When a further usage of the catheter is prohibited or impermissible, the verification module 208, in step 616, disables the base unit and prevents usage of the catheter. A signal may be provided to the operator that the currently coupled catheter may not be used, why the catheter may not be used, and/or that a new catheter must be coupled to the base unit. When a further usage of the catheter is permissible, the verification module 208, in step 620, enables the base unit to energize the catheter and updates data structures in base unit memory associated with historic usage the catheter.

Figure 7:
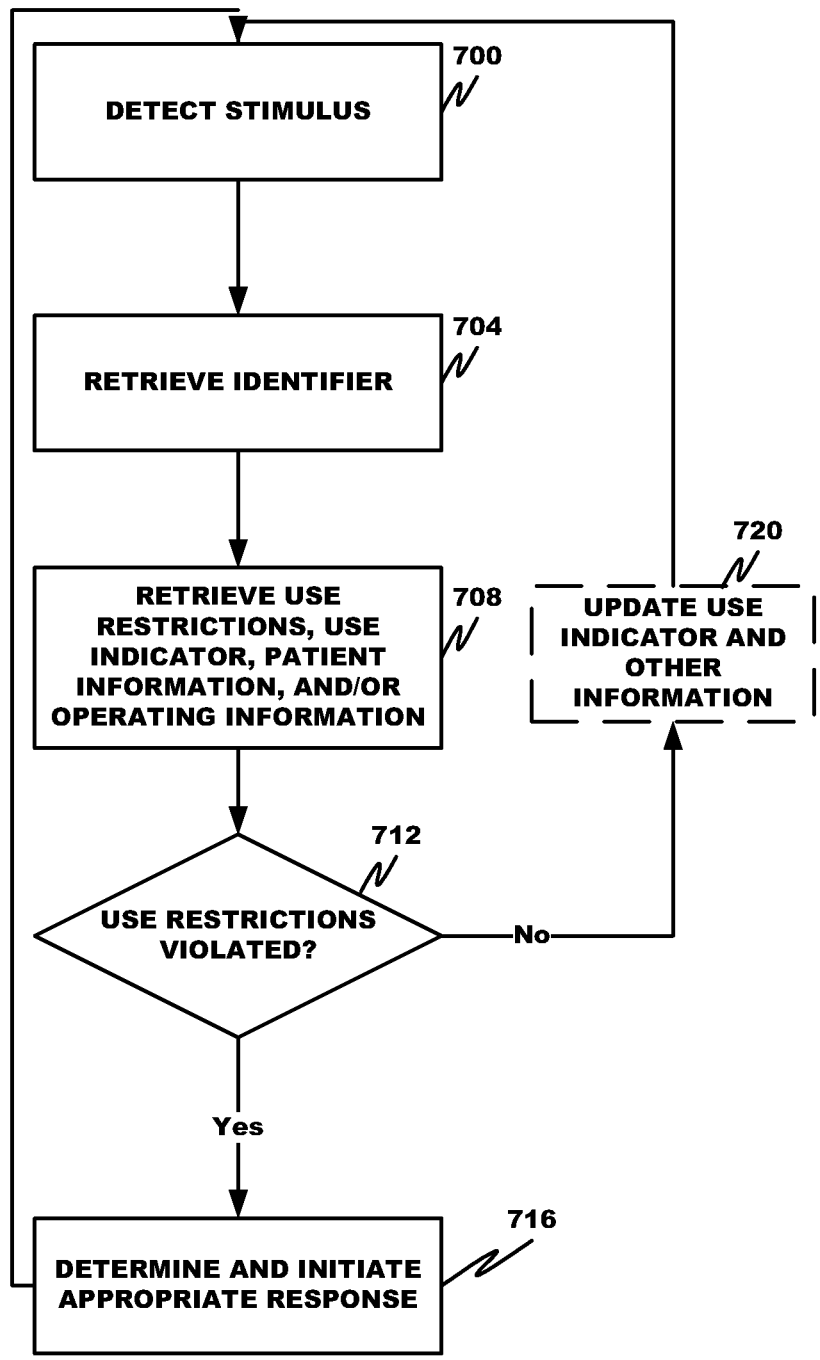
FIG. 7 depicts logic for the verification module according to an embodiment.

A further operational embodiment is shown in FIG. 7. In this embodiment, the identifier is unique to the corresponding catheter and the identification module includes the information referenced in FIG. 8.

In step 700, the verification module 208 detects a stimulus. The stimulus can be, for example, any of the stimuli referenced above.

In step 704, the identification module 208 retrieves, via the reader 204, the identifier.

In step 708, the verification module 208 retrieves, via the reader 204 and from memory 200, a use indicator 808, set of use restrictions 812, patient information 816, and operating information 820.

In decision diamond 712, the verification module 208 determines whether enabling the catheter would violate a use restriction. For example, the use indicator may indicate that further usage of the catheter is prohibited. By way of further example, the verification module 208 may need to compare the historic usage information associated with and/or contained within the use indicator against the set of usage restrictions to determine whether further usage of the catheter is permitted.

When a further usage of the catheter is prohibited or impermissible, the verification module 208, in step 716, disables the base unit, thereby preventing usage of the catheter, and determines and initiates an appropriate response. Which response is appropriate may depend on the stimulus. Suitable responses include one or more of an audible alarm, a visual warning (such as a flashing light), an audible or visual message provided to the user on a user interface (not shown) of the base unit, terminating or pausing of an initialization routine to commence catheter energization, and providing information surrounding the incident to the catheter manufacturer and/or healthcare personnel. The information can include not only the information received from the identification module and base unit memories but also a unique identifier of the base unit to enable the manufacturer to identify who is potentially misusing the catheter. This information could be provided to the manufacturer in substantial real time or when the base unit is updated and/or repaired.

When a further usage of the catheter is permissible, the verification module 208, in step 720, enables the base unit to energize the catheter and updates the use indicator and other information in the memory 800 of the identification module 200.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

The exemplary systems and methods of this disclosure have been described in relation to an endovascular device. However, to avoid unnecessarily obscuring the present disclosure, the preceding description omits a number of known structures and devices. This omission is not to be construed as a limitation of the scopes of the claims. Specific details are set forth to provide an understanding of the present disclosure. It should however be appreciated that the present disclosure may be practiced in a variety of ways beyond the specific detail set forth herein.

Furthermore, while the exemplary aspects, embodiments, and/or configurations illustrated herein show the various components of the system collocated, certain components of the system can be located remotely, at distant portions of a distributed network, such as a LAN and/or the Internet, or within a dedicated system. Thus, it should be appreciated, that the components of the system can be combined in to one or more devices, such as a base unit and/or coupler, or collocated on a particular node of a distributed network, such as an analog and/or digital telecommunications network, a packet-switch network, or a circuit-switched network. It will be appreciated from the preceding description, and for reasons of computational efficiency, that the components of the system can be arranged at any location within a distributed network of components without affecting the operation of the system.

Furthermore, it should be appreciated that the various links connecting the elements can be wired or wireless links, or any combination thereof, or any other known or later developed element(s) that is capable of supplying and/or communicating data to and from the connected elements. These wired or wireless links can also be secure links and may be capable of communicating encrypted information. Transmission media used as links, for example, can be any suitable carrier for electrical signals, including coaxial cables, copper wire and fiber optics, and may take the form of acoustic or light waves, such as those generated during radio-wave and infra-red data communications.

Also, while the flowcharts have been discussed and illustrated in relation to a particular sequence of events, it should be appreciated that changes, additions, and omissions to this sequence can occur without materially affecting the operation of the disclosed embodiments, configuration, and aspects.

A number of variations and modifications of the disclosure can be used. It would be possible to provide for some features of the disclosure without providing others.

For example, the verification module can indicate that a catheter may no longer be used by erasing all or part of its memory. In that manner, no identifier is present to enable catheter usage.

In another example, information stored on the identification module is accessed directly by the verification module via one or more pins in electrical communication with the identification module. In this configuration, no reader is present.

In another example, the identification module is used in conjunction with the pin signaling and look up tables of the prior art by which the catheter is identified to the base unit. For example, part of the identifier can be provided by pin signaling and the other part of the identifier can be provided by some other transmission medium.

In yet another example, the systems and methods of this disclosure can be implemented in conjunction with a special purpose computer, a programmed microprocessor or microcontroller and peripheral integrated circuit element(s), an ASIC or other integrated circuit, a digital signal processor, a hard-wired electronic or logic circuit such as discrete element circuit, a programmable logic device or gate array such as PLD, PLA, FPGA, PAL, special purpose computer, any comparable means, or the like. In general, any device(s) or means capable of implementing the methodology illustrated herein can be used to implement the various aspects of this disclosure. Exemplary hardware that can be used for the disclosed embodiments, configurations and aspects includes computers, handheld devices, telephones (e.g., cellular, Internet enabled, digital, analog, hybrids, and others), and other hardware known in the art. Some of these devices include processors (e.g., a single or multiple microprocessors), memory, nonvolatile storage, input devices, and output devices. Furthermore, alternative software implementations including, but not limited to, distributed processing or component/object distributed processing, parallel processing, or virtual machine processing can also be constructed to implement the methods described herein.

In yet another embodiment, the disclosed methods may be readily implemented in conjunction with software using object or object-oriented software development environments that provide portable source code that can be used on a variety of computer or workstation platforms. Alternatively, the disclosed system may be implemented partially or fully in hardware using standard logic circuits or VLSI design. Whether software or hardware is used to implement the systems in accordance with this disclosure is dependent on the speed and/or efficiency requirements of the system, the particular function, and the particular software or hardware systems or microprocessor or microcomputer systems being utilized.

In yet another embodiment, the disclosed methods may be partially implemented in software that can be stored on a storage medium, executed on programmed general-purpose computer with the cooperation of a controller and memory, a special purpose computer, a microprocessor, or the like. In these instances, the systems and methods of this disclosure can be implemented as program embedded on personal computer such as an applet, JAVA® or CGI script, as a resource residing on a server or computer workstation, as a routine embedded in a dedicated measurement system, system component, or the like. The system can also be implemented by physically incorporating the system and/or method into a software and/or hardware system.

Although the present disclosure describes components and functions implemented in the aspects, embodiments, and/or configurations with reference to particular standards and protocols, the aspects, embodiments, and/or configurations are not limited to such standards and protocols. Other similar standards and protocols not mentioned herein are in existence and are considered to be included in the present disclosure. Moreover, the standards and protocols mentioned herein and other similar standards and protocols not mentioned herein are periodically superseded by faster or more effective equivalents having essentially the same functions. Such replacement standards and protocols having the same functions are considered equivalents included in the present disclosure.

The present disclosure, in various aspects, embodiments, and/or configurations, includes components, methods, processes, systems and/or apparatus substantially as depicted and described herein, including various aspects, embodiments, configurations embodiments, subcombinations, and/or subsets thereof. Those of skill in the art will understand how to make and use the disclosed aspects, embodiments, and/or configurations after understanding the present disclosure. The present disclosure, in various aspects, embodiments, and/or configurations, includes providing devices and processes in the absence of items not depicted and/or described herein or in various aspects, embodiments, and/or configurations hereof, including in the absence of such items as may have been used in previous devices or processes, e.g., for improving performance, achieving ease and\or reducing cost of implementation.

The foregoing discussion has been presented for purposes of illustration and description. The foregoing is not intended to limit the disclosure to the form or forms disclosed herein. In the foregoing Detailed Description for example, various features of the disclosure are grouped together in one or more aspects, embodiments, and/or configurations for the purpose of streamlining the disclosure. The features of the aspects, embodiments, and/or configurations of the disclosure may be combined in alternate aspects, embodiments, and/or configurations other than those discussed above. This method of disclosure is not to be interpreted as reflecting an intention that the claims require more features than are expressly recited in each claim. Rather, as the following claims reflect, inventive aspects lie in less than all features of a single foregoing disclosed aspect, embodiment, and/or configuration. Thus, the following claims are hereby incorporated into this Detailed Description, with each claim standing on its own as a separate preferred embodiment of the disclosure.

Moreover, though the description has included description of one or more aspects, embodiments, and/or configurations and certain variations and modifications, other variations, combinations, and modifications are within the scope of the disclosure, e.g., as may be within the skill and knowledge of those in the art, after understanding the present disclosure. It is intended to obtain rights which include alternative aspects, embodiments, and/or configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method, comprising:
   detecting, by a microprocessor executable verification module in a base unit from an endovascular device, a stimulus,
   upon detecting the stimulus, the microprocessor executable verification module receiving from the endovascular device, an identifier of the endovascular device, a use indicator, a use restriction, and operating information, wherein the identifier is indicative of a type of procedure for which the endovascular device can be used; and
   based on the use indicator and the use restriction, determining whether to configure the base unit to operate the endovascular device; and
   upon determining to configure the base unit to operate the endovascular device, based on the identifier, the verification module configuring the endovascular device for use;
   wherein the identifier, use indicator and use restriction are provided wirelessly by the endovascular device to the verification module, wherein the verification module, upon configuring the base unit to operate the endovascular device, uses the operating information to operate the endovascular device, wherein the operating information is stored in a memory of the endovascular device, wherein the endovascular device is a laser catheter, and wherein the operating information comprises two or more of a physical dimension of the laser catheter, an active area of the laser catheter, a maximum allowable fluence of the laser catheter, a minimum allowable fluence of the laser catheter, a repetition rate of the laser catheter, and a lasing train time of the laser catheter.

2. The method of claim 1, wherein the identifier is unrelated to a configuration of a connector of the laser catheter to a coupler of the base unit.

3. The method of claim 1, wherein the verification module uses the identifier to determine whether the laser catheter can be enabled for use and, when the identifier cannot be enabled for use, disables the base unit from energizing the laser catheter.

4. The method of claim 1, wherein the identifier is contained in the memory of the laser catheter, wherein the memory of the laser catheter is in a radio frequency identification tag, and wherein the base unit further comprises a radio frequency identification tag reader.

5. The method of claim 1, wherein the identifier is unique to the corresponding laser catheter.

6. The method of claim 1, wherein the identifier is common to a first plurality of laser catheters but different than an identifier associated with a second plurality of laser catheters.

7. The method of claim 1, wherein the identifier is contained in the memory of the laser catheter and wherein the laser catheter comprises in memory not only the identifier but also patient information.

8. A system, comprising:
a microprocessor executable verification module in a base unit configured to couple to an endovascular device, whereupon the endovascular device coupling to the base unit, the microprocessor executable verification module receives a stimulus;
a microprocessor readable identifier of the endovascular device in a memory of the endovascular device;
a microprocessor readable use indicator and use restriction of the endovascular device in the memory of the endovascular device, wherein the microprocessor readable use indicator is indicative of a type of procedure for which the endovascular device can be used; and
whereupon receiving the stimulus, the microprocessor executable verification module, based on the use indicator and the use restriction, determines whether the endovascular device can be enabled for use;
wherein the identifier, use indicator and use restriction are provided wirelessly by the endovascular device to the verification module, wherein the verification module, upon determining the endovascular device can be enabled for use, configures the endovascular device for use, and wherein the verification module uses the identifier to determine an appropriate set of operating information for the endovascular device, wherein the operating information is stored in the memory of the endovascular device, and wherein the endovascular device is a laser catheter, and wherein the operating information comprises two or more of a physical dimension of the laser catheter, an active area of the laser catheter, a maximum allowable fluence of the laser catheter, a minimum allowable fluence of the laser catheter, a repetition rate of the laser catheter, and a lasing train time of the laser catheter.

9. The system of claim 8, wherein the identifier is unrelated to a configuration of a connector of the laser catheter to a coupler of the base unit.

10. The system of claim 8, wherein the verification module, upon determining the endovascular device cannot be enabled for use, disables the base unit from energizing the laser catheter.

11. The system of claim 8, wherein the memory of the laser catheter is in a radio frequency identification tag and wherein the base unit further comprises a radio frequency identification tag reader.

12. The system of claim 8, wherein the identifier is unique to the corresponding laser catheter.

13. The system of claim 8, wherein the identifier is common to a first plurality of laser catheters but different than an identifier associated with a second plurality of laser catheters.

14. The system of claim 8, wherein the laser catheter comprises in memory not only the identifier but also patient information.

15. A tangible and non-transient computer readable medium in a base unit configured to couple to an endovascular device and comprising microprocessor readable and executable instructions that, when executed:
receive a stimulus upon the endovascular device being coupled to the base unit;
access an identifier of the endovascular device, the identifier being located at the endovascular device;
access a use indicator and a use restriction, wherein the use indicator is indicative of a type of procedure for which the endovascular device can be used;
based upon the use indicator and the use restriction, determining whether to configure the base unit to operate the endovascular device; and
upon determining to configure the base unit to operate the endovascular device, based on the identifier, at least one of configure the endovascular device for use and determine whether the endovascular device can be enabled for use, and based on the use indicator determine whether the endovascular device can be used for the type of procedure;
wherein the identifier is provided wirelessly by the endovascular device to a verification module, wherein the verification module, based on the identifier and the use indicator, configures the endovascular device for use and wherein the verification module uses the identifier to determine an appropriate set of operating information for the endovascular device, wherein the identifier is contained in a memory of the endovascular device, wherein the endovascular device is a laser catheter, wherein the operating information is stored in the memory of the laser catheter, and wherein the operating information comprises two or more of a physical dimension of the laser catheter, an active area, a maximum allowable fluence, a minimum allowable fluence, a repetition rate, and a lasing train time.

16. The computer readable medium of claim 15, wherein the identifier is unrelated to a configuration of a connector of the laser catheter to a coupler of the base unit.

17. The computer readable medium of claim 15, wherein the verification module uses the identifier to determine whether the laser catheter can be enabled for use and, when the identifier cannot be enabled for use, disables the base unit from energizing the laser catheter.

18. The computer readable medium of claim 15, wherein the memory of the laser catheter is in a radio frequency identification tag, and wherein the base unit further comprises a radio frequency identification tag reader.

19. The computer readable medium of claim 15, wherein the identifier is unique to the corresponding laser catheter.

20. The computer readable medium of claim 15, wherein the identifier is common to a first plurality of laser catheters but different than an identifier associated with a second plurality of laser catheters.

21. The computer readable medium of claim 15, wherein the laser catheter comprises in memory not only the identifier but also patient information.

\* \* \* \* \*

UNITED STATES PATENT AND TRADEMARK OFFICE
CERTIFICATE OF CORRECTION

PATENT NO. : 9,757,200 B2
APPLICATION NO. : 13/804812
DATED : September 12, 2017
INVENTOR(S) : Magee et al.

Page 1 of 2

It is certified that error appears in the above-identified patent and that said Letters Patent is hereby corrected as shown below:

On the Title Page

On Page 3, in item (56), under "OTHER PUBLICATIONS", in Column 2, Line 49, delete "Actualtors" and insert -- Actuators --, therefor.

On Page 3, in item (56), under "OTHER PUBLICATIONS", in Column 2, Line 62, delete "Tomogrpahy;" and insert -- Tomography; --, therefor.

On Page 3, in item (56), under "OTHER PUBLICATIONS", in Column 2, Line 66, delete "Europace 9 ," and insert -- Europace 9, --, therefor.

On Page 4, in item (56), under "OTHER PUBLICATIONS", in Column 1, Line 22, delete "Manufacturing; ;" and insert -- Manufacturing; --, therefor.

On Page 4, in item (56), under "OTHER PUBLICATIONS", in Column 2, Line 17, delete "Capability ;" and insert -- Capability; --, therefor.

On Page 4, in item (56), under "OTHER PUBLICATIONS", in Column 2, Line 47, delete "Let US" and insert -- Let Us --, therefor.

On Page 5, in item (56), under "OTHER PUBLICATIONS", in Column 2, Line 12, delete "Automaton," and insert -- Automation, --, therefor.

On Page 6, in item (56), under "OTHER PUBLICATIONS", in Column 1, Line 7, delete "Evaluaton" and insert -- Evaluation --, therefor.

On Page 6, in item (56), under "OTHER PUBLICATIONS", in Column 1, Line 22, delete "Transesophagael" and insert -- Transoesophageal --, therefor.

Signed and Sealed this
Thirteenth Day of March, 2018

Andrei Iancu
*Director of the United States Patent and Trademark Office*

CERTIFICATE OF CORRECTION (continued)
U.S. Pat. No. 9,757,200 B2

On Page 6, in item (56), under "OTHER PUBLICATIONS", in Column 2, Line 33, delete "Alowance" and insert -- Allowance --, therefor.

In the Specification

In Column 1, Lines 53-54, delete "transmission" and insert -- transmission. --, therefor.

In Column 2, Line 15, delete "device and" and insert -- device; and --, therefor.

In Column 3, Line 67, delete "and EPROM," and insert -- an EPROM, --, therefor.

In Column 11, Line 17, delete "usage the" and insert -- usage of the --, therefor.

In Column 11, Line 26, delete "identification module 208" and insert -- identification module 200 --, therefor.

In Column 11, Line 29, delete "memory 200," and insert -- memory 220, --, therefor.

In Column 12, Line 22, delete "in to" and insert -- into --, therefor.

In Column 14, Line 11, delete "and\or" and insert -- and/or --, therefor.